(12) United States Patent
Mathiesen et al.

(10) Patent No.: US 10,258,576 B2
(45) Date of Patent: *Apr. 16, 2019

(54) PARTICULATE COMPRISING A CALCIUM-CONTAINING COMPOUND AND A SUGAR ALCOHOL

(75) Inventors: Jacob Mathiesen, Hobro (DK); Carsten Martini Nielsen, Søborg (DK); Peder Mohr Olsen, Kirke Hyllinge (DK); Poul Egon Bertelsen, Roskilde (DK)

(73) Assignee: Takeda AS, Asker (NO)

( * ) Notice: Subject to any disclaimer, the term of this patent is extended or adjusted under 35 U.S.C. 154(b) by 945 days.

This patent is subject to a terminal disclaimer.

(21) Appl. No.: 11/597,454

(22) PCT Filed: May 24, 2005

(86) PCT No.: PCT/DK2005/000338
§ 371 (c)(1),
(2), (4) Date: Jul. 10, 2007

(87) PCT Pub. No.: WO2005/115342
PCT Pub. Date: Dec. 8, 2005

(65) Prior Publication Data
US 2008/0175904 A1 Jul. 24, 2008

(30) Foreign Application Priority Data
May 24, 2004 (DK) ................................. 2004 00813

(51) Int. Cl.
*A61K 9/20* (2006.01)
*A61K 9/00* (2006.01)
*A61K 9/16* (2006.01)

(52) U.S. Cl.
CPC .......... *A61K 9/2077* (2013.01); *A61K 9/0056* (2013.01); *A61K 9/1623* (2013.01); *A61K 9/2004* (2013.01); *A61K 9/2018* (2013.01)

(58) Field of Classification Search
CPC .. A61K 9/2077; A61K 9/0056; A61K 9/1623; A61K 9/2004; A61K 9/2018
USPC .......................................................... 424/464
See application file for complete search history.

(56) References Cited

U.S. PATENT DOCUMENTS

| | | | |
|---|---|---|---|
| 4,684,534 A | 8/1987 | Valentine | |
| 4,830,859 A | 5/1989 | Finnan et al. | |
| 5,108,728 A | 4/1992 | Rau et al. | |
| 5,348,745 A | 9/1994 | Daher | |
| 5,853,759 A * | 12/1998 | Katdare et al. | ............... 424/466 |
| 6,149,941 A | 11/2000 | Schwarz et al. | |
| 6,475,510 B1 | 11/2002 | Venkatesh et al. | |
| 2003/0190369 A1 | 10/2003 | Lovett | |
| 2003/0194440 A1 | 10/2003 | Lofroth et al. | |
| 2003/0211168 A1 | 11/2003 | Lynenskjold et al. | |
| 2004/0071772 A1 | 4/2004 | Narita et al. | |
| 2004/0166162 A1 * | 8/2004 | Niecestro et al. | ............ 424/472 |

FOREIGN PATENT DOCUMENTS

| | | |
|---|---|---|
| DE | 20216314 U1 | 12/2003 |
| EP | 0054333 A1 | 6/1982 |
| EP | 0265951 A2 | 5/1988 |
| EP | 0647591 A1 | 4/1995 |
| EP | 0 872 240 A1 | 10/1998 |
| EP | 0914818 A1 | 5/1999 |
| EP | 1126017 A1 | 8/2001 |
| EP | 1369131 A1 | 12/2003 |
| FR | 2 717 389 | 9/1995 |
| FR | 2724844 A1 | 3/1996 |
| JP | 5306229 A | 11/1993 |
| JP | 2001-316249 A | 11/2001 |
| JP | 2002-518291 | 6/2002 |
| JP | 2002-529438 A | 9/2002 |
| WO | 8102521 A1 | 9/1981 |
| WO | WO-92/10168 A1 | 6/1992 |
| WO | WO-95/08273 A1 | 3/1995 |
| WO | WO-96/09036 A1 | 3/1996 |
| WO | WO-97/41835 A1 | 11/1997 |
| WO | WO-98/52541 | 11/1998 |
| WO | WO-99/06051 A1 | 2/1999 |
| WO | WO 99/08659 | 2/1999 |
| WO | 9932092 A1 | 7/1999 |
| WO | WO 00-28973 | 5/2000 |
| WO | WO-00/28973 | 5/2000 |
| WO | WO 00/28973 * | 5/2000 ............... A61K 9/16 |
| WO | WO-00/28973 A1 | 5/2000 |

(Continued)

OTHER PUBLICATIONS

NeosorbP100T product specification. Located at http://www.signetchem.com/downloads/datasheets/roquette/Neosorb-P-100-T-sorbitol-specifications.pdf—accessed Jun. 22, 2009.*

(Continued)

*Primary Examiner* — Adam C Milligan
(74) *Attorney, Agent, or Firm* — Mintz Levin Cohn Ferris Glovsky and Popeo, P.C.; Peter F. Corless

(57) ABSTRACT

The present invention relates to a particulate material and a solid dosage form notably tablets comprising a regularly shaped calcium-containing compound such as a calcium salt as a therapeutically and/or prophylactically active substance and a pharmaceutically acceptable sugar alcohol such as, e.g., sorbitol and/or isomalt that has a micro structure as evidenced by SEM. The invention also relates to a process for the preparation of the particulate material and solid dosage form. The process involves agglomeration of the calcium-containing compound and the pharmaceutically acceptable sugar alcohol by means of roller compaction. The particulate material obtained by roller compaction is suitable for use in the further processing of the particulate material into e.g. tablets such as chewing tablets.

25 Claims, 26 Drawing Sheets

(56) References Cited

FOREIGN PATENT DOCUMENTS

| WO | WO-00/76650 A1 | 12/2000 |
| WO | WO-01/83374 A2 | 11/2001 |
| WO | 03/055500 A1 | 7/2003 |

OTHER PUBLICATIONS

Overgaard, Patients' evaluation of shape, size, and colour of solid dosage forms, Pharmacy World & Science, vol. 23, No. 5, pp. 185-188, 2001.*
"2.9.8. Resistance to Crushing of Tablets" European Pharmacopoeia 7.0 p. 267 Jan. 2008:20908.
"2.9.3. Dissolution Test for Solid Dosage Forms" European Pharmacopoeia 7.0 pp. 256-263 Jan. 2010:20903 corrected 6.8.
"2.9.7. Friability of Uncoated Tablets" European Pharmacopoeia 7.0 p. 266 Jan. 2010:20907.
"2.9.1. Disintegration of Tablets and Capsules" European Pharmacopoeia 7.1 pp. 3331-3332 Apr. 2011:20901.
Klobes P et al. "Porosity and Specific Surface Area Measurements for Solid Materials" NIST, (SP 960-17).
Bolhuis et al., "DC Calcium lactate, a new filler-binder for direct compaction of tablets", International Journal of Pharmaceuticals, vol. 221, 2001, pp. 77-86.
Bruynseels, et al., "Fluidized-bed process fully established and still developing", Nitrogen No. 183, Jan.-Feb. 1990, pp. 22-26.
CPhI Celebrates ten years of growth in Frankfurt—Manufacturing Chemist, Dec. 31, 1999.
Oneda et al., "The effect of formulation variables on the dissolution and physical properties of spray-dried microspheres containing organic salts", Power Technology, vol. 130, 2003, pp. 377-384.
Rumpler et al., "Continuous Agglomeration and Granulation by Fluidization", Food Marketing & Technology, Apr. 1999, pp. 1-3.
Japanese Office Action from corresponding Japanese Patent Application No. 2007-513680, Mar. 13, 2012.
"Excipient Systems", http://www.merck.de/english/services/specialchemie/s_chn/pharma/excipients.htm (Nov. 7, 2000).
Merck Formaxx products—marketing information (Sep. 16, 2004).

* cited by examiner

Use of intra-granuar, extra granular sorbitol or no sobitol as binder.
Investigation of tablet hardess as a function of compression pressure.

Impact of compaction force on particle size distribution.

Impact on tablet hardness of variations in particle size distriburtion of granulate.

Variation in particle size of sorbitol
Investigation of tablet hardness as a function of compression pressure Impact of moisture content of surrounding air on tablet hardness.

Impact on tablet hardness of variations in form of Calcium crystals

Impact on tablet hardness of omitting lumb breaking of 38μm sorbitol.

Impact on tablet hardness of admixing of PVP30

Calcium source: Scoralite - Impact of type and particle size of sugar alcohol

Calcium source: Merck 2064 - Impact of type and particle size of sugar alcohol
Reference: Scoralite Calcium source: Scoralite - Impact of extra granular admixture of sugar sorbitol of different particle size. Reference: Intragranular addition of sorbitol.

Impact on granular particle size of intra or extra granular admixture of sorbitol.
Calcium source: Scorelite

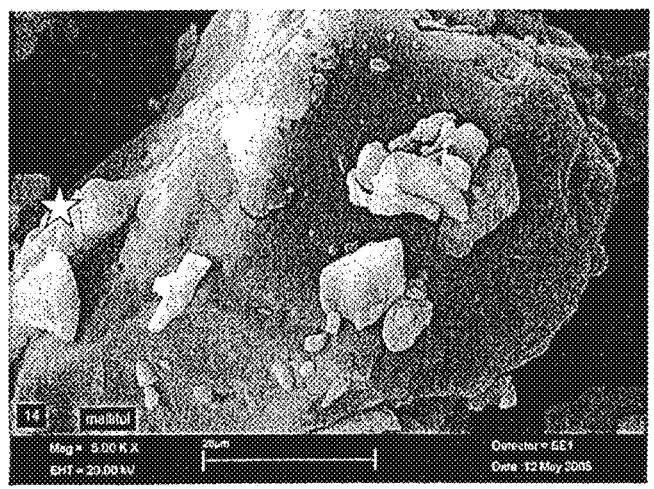
The breakline indicated by the cross is caused by local heating during microscopy.
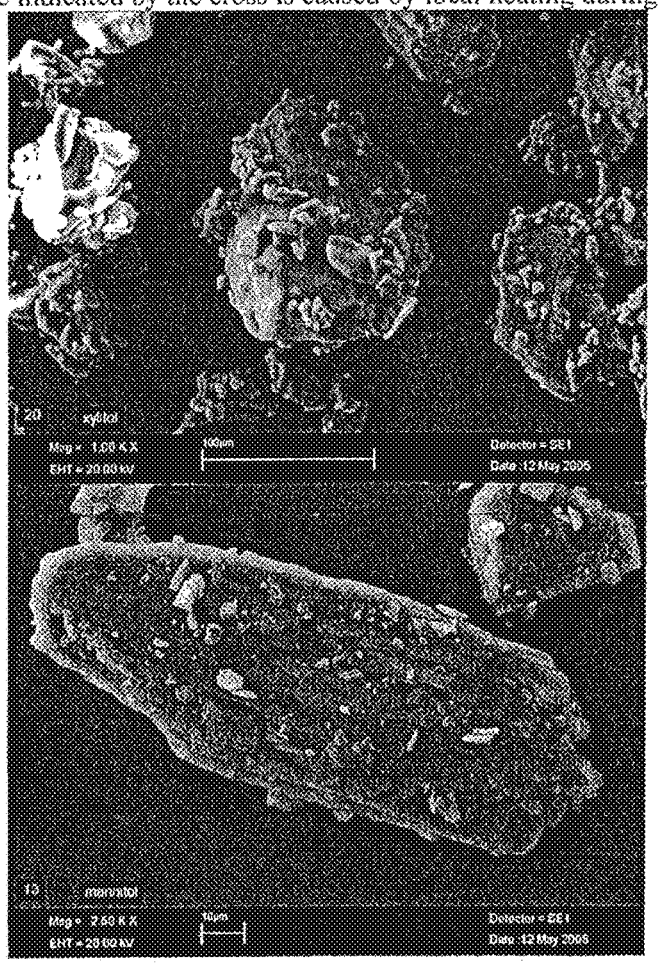
Fig. 17

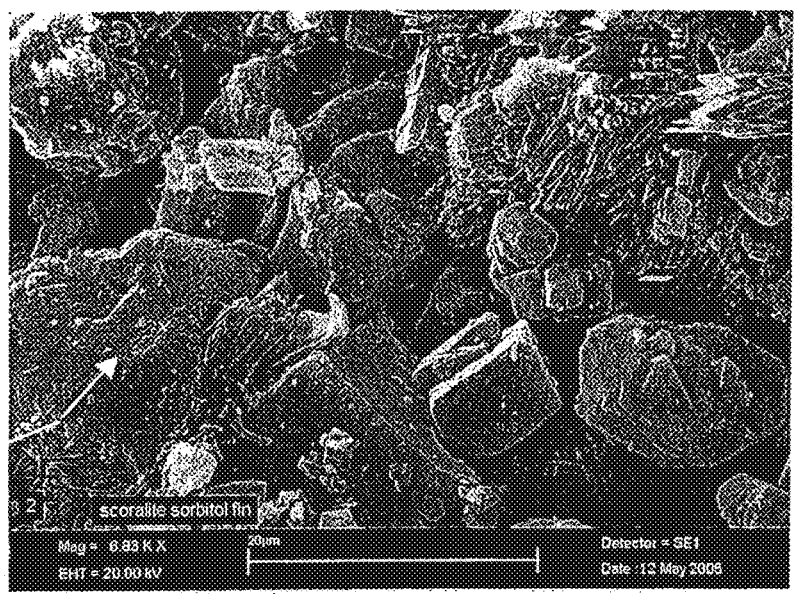
Arrows marking sorbitol binding calcium carbonate crystals
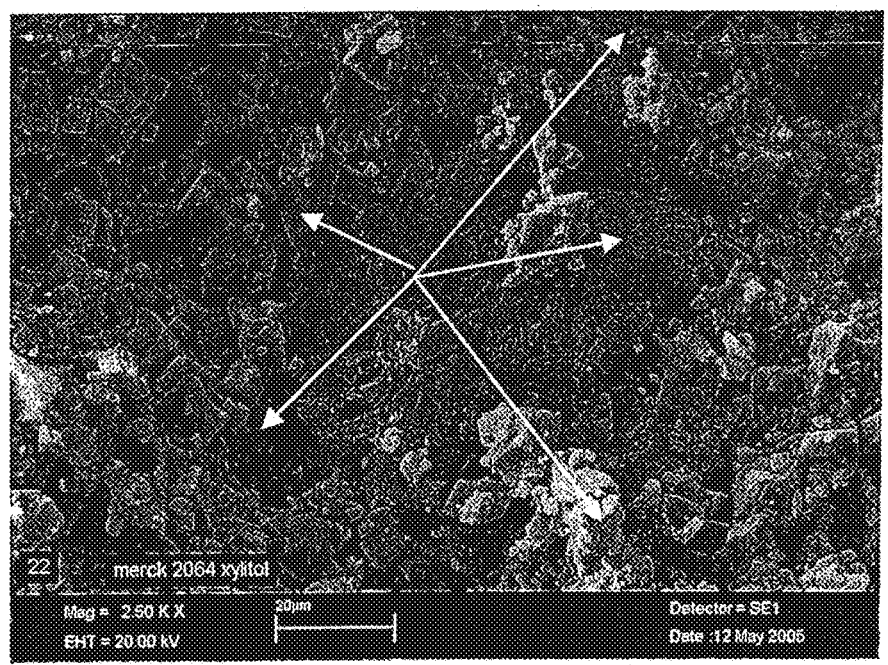
Arrows marking extent of a xylitol particle
Fig. 18

Impact of mixing time on crushing strength stability at 25°C/60%RH

FIG. 26A
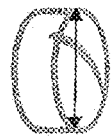
FIG. 26B
FIG. 26C
FIG. 26D
FIG. 26E
Fig. 26

PARTICULATE COMPRISING A CALCIUM-CONTAINING COMPOUND AND A SUGAR ALCOHOL

FIELD OF THE INVENTION

The present invention relates to a particulate material and a solid dosage form notably tablets comprising a regularly shaped calcium-containing compound such as a calcium salt as a therapeutically and/or prophylactically active substance and a pharmaceutically acceptable sugar alcohol such as, e.g., sorbitol and/or isomalt that has a micro structure as evidenced by SEM. The invention also relates to a process for the preparation of the particulate material and solid dosage form. The process involves agglomeration of the calcium-containing compound and the pharmaceutically acceptable sugar alcohol by means of roller compaction. The particulate material obtained by roller compaction is suitable for use in the further processing of the particulate material into e.g. tablets such as chewing tablets.

The present invention is based on the findings that the result of an agglomeration process by which a calcium-containing compound is agglomerated depends on the particular shape of the calcium-containing compound and the micro structure of the material used as a binder in the agglomeration process.

BACKGROUND

Calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellular calcium levels (Burgoyne R D. Biochim Biophys Acta 1984; 779: 201-16). The secretion of hormones and the activity of key enzymes and proteins are dependent on calcium. Finally calcium as a calcium phosphate complex confers rigidity and strength on the skeleton (Boskey A L. Springer, 1988: 171-26). Because bone contains over 99% of the total body calcium, skeletal calcium also serves as the major long-term calcium reservoir.

Calcium salts such as, e.g., calcium carbonate is used as a source of calcium especially for patients suffering from or at risk of osteoporosis. Moreover, calcium carbonate is used as an acid-neutralizing agent in antacid tablets.

Furthermore, calcium may have anticancer actions within the colon. Several preliminary studies have shown high calcium diets or intake of calcium supplementation is associated with reduced colon rectal cancer. There is increasing evidence that calcium in combination with acetylsalicylic acid (ASA) and other non-steroidal anti-inflammatory drugs (NSAIDS) reduce the risk the risk of colorectal cancer.

Recent research studies suggest that calcium might relieve premenstrual syndrome (PMS). Some researchers believe that disruptions in calcium regulation are an underlying factor in the development of PMS symptoms. In one study, half the women of a 466 person group of pre-menopausal women from across the U.S. were tracked for three menstrual cycles and were given 1200 mg of calcium supplements daily throughout the cycle. The final results showed that 48% of the women who took placebo had PMS related symptoms. Only 30% of those receiving calcium tablet did.

Calcium salts like e.g. calcium carbonate is used in tablets and due to the high dose of calcium required, such tablets are often in the form of chewable tablets. It is a challenge to formulate chewable tablets containing a calcium salt, which tablets have a pleasant taste and an acceptable mouthfeel without the characteristic dominating taste or feeling of chalk.

Furthermore, i) the high dose of calcium carbonate (normally 300-600 mg of elemental calcium twice daily, corresponding to 750-1500 mg of calcium carbonate twice daily), ii) the inherent poor properties of regular shaped calcium carbonate with respect to tabletting properties like compressibility, which accordingly calls for the need of adding one or more pharmaceutically acceptable excipients in order to obtain a suitable compressibility, and iii) the extremely bad taste or mouthfeel of a calcium salt itself especially with respect to chalkiness make it very difficult to prepare a tablet that has a suitable small size, which is conveniently small for a patient. Sufficient taste masking is another major challenge when formulating chewable tablets.

The present inventors have found an easy way for producing e.g. chewable tablets containing a physiologically tolerable calcium-containing compound by using a granulate comprising agglomerates of the calcium-containing compound. The granulate is obtained without use of any solvent (e.g. water), but involves the technique of roller compaction of the calcium-containing compound to form agglomerates having suitable properties for further processing into a solid dosage form such as, e.g., tablets.

EP 0 054 333 (Stauffer Chemical Company) describes a process of compacting fine particles of calcium phosphate by means of roller compacting to obtain a powder. The powder obtained has a larger bulk density than the starting material, which makes it suitable for use as an excipient in producing pharmaceutical tablets. In contrast to EP 0 054 333 the present invention does not employ roller compaction with the aim of increasing the bulk density of a pharmaceutically acceptable excipient, but as a novel method for agglomeration, i.e. for building up agglomerates of particles in order to increase the mean particle size to a size that is suitable for further processing of the material into e.g. tablets such as, e.g., chewable tablets that have an acceptable taste and/or mouthfeel.

Previously it has been described that the quality of the calcium-containing compound as well as the method for preparation of a pharmaceutical composition containing the calcium-containing compound are of great importance in order to obtain acceptable taste and mouthfeel of a chewable tablet (WO 00/28973). In contrast to WO 00/28973 the method according to the invention does not employ a step of binding the particles together by a wet granulation process, which means that the method according to the invention advantageously can be employed when it is desired to incorporate substances that are sensitive towards humidity. An example of such a substance is vitamin D that often is included together with a calcium salt in a pharmaceutically dosage form. The present invention provides a simple and cost-effective alternative method to obtain such a dosage form without the need of a step e.g. involving wet granulation.

DESCRIPTION OF THE INVENTION

It has surprisingly been found that roller compaction of a calcium-containing compound together with a pharmaceutically acceptable sugar alcohol that has binding properties improves the properties for pharmaceutical use of the compacts obtained thereby.

As mentioned above, in the present context the process of roller compacting of a powder is applied as an alternative method to known granulation or agglomeration methods, i.e. wet granulation or—when tablets are prepared—direct compression using dry binders. The present inventors have found that the process of roller compacting is a very mild method that does not destroy the possibility of obtaining products that have an acceptable mouthfeel and at the same time are without a dominating chalk-like taste or feel. Normally, roller compaction is employed with the purpose of increasing the bulk density of a particular substance or composition e.g. in order to transform a bulky material to a less voluminous material that is easier to use in the manufacturing of pharmaceutical compositions. To the best of the present inventor's knowledge, roller compaction has not been employed as a gentle granulation process that maintains or do not destroy important properties of the material (i.e. the calcium-containing compound) so that an acceptable taste, mouthfeel etc. can be obtained.

With an aim of preparing a smaller tablet that still has acceptable taste and mouthfeel, the present inventors have found that the use pharmaceutically acceptable sugar alcohols as binding material in the agglomeration process is particularly suitable. However, in order to obtain suitable properties of a roller compacted composition containing a calcium-containing compound, two major factors are important, namely the properties of the calcium-containing compound itself and the choice of sugar alcohol used as a binder in the agglomeration process. To this end the present inventors have found that when a regularly shaped calcium-containing compound is used, which has very poor compressibility properties itself, then—in order to obtain an acceptable end result—it is very important that the sugar alcohol used has a micro structure, i.e. a structure that enables a certain deformation and sufficient distribution throughout the tablet during the roller compaction process in order to establish sufficient bonding between the individual calcium (and sugar alcohol) particles.

In the present context, the term "regularly shaped" in connection with a calcium-containing compound is intended to denote that the individual particles as evidenced by SEM have a rounded or smooth-like surface like e.g. the cubic-formed crystals shown in FIG. 15 herein. The regular shape results in a relatively low specific surface area, that is below 1.5 m$^2$/g In the present context, the term "micro structure" used in connection with sugar alcohols is intended to denote that a single crystal of the sugar alcohol is a polycrystal such as multiple crystals or fiber crystals comprising smaller units, i.e. the crystals have an identifiable substructure that is detectable by SEM (e.g. see FIG. 16 herein). The micro structure enables a certain deformation and sufficient distribution throughout the tablet during the roller compaction process in order to establish sufficient bonding between the individual calcium (and sugar alcohol) particles. Furthermore, a sufficient compressibility is required, cf. the examples herein.

Moreover, in contrast to what is general knowledge within the field of pharmaceutical formulation, the present inventors have found that a sugar alcohol like sorbitol is not suitable for use in the standard quality generally recommended. This quality has a mean particle size of about 300 μm, but as demonstrated in the examples herein such a mean particle size is too large in order to enable a sufficient distribution of sorbitol particles around the particles of the calcium-containing compound resulting in tablets having unacceptable properties with respect to crushing strength. The particle size of e.g. sorbitol must be much smaller in order to obtain good and acceptable results with respect to crushing strength.

Accordingly, the pharmaceutically acceptable sugar alcohol employed according to the invention has a mean particle size of at the most about 150 μm such as, e.g., at the most about 110 μm, at the most about 100 μm, at the most about 90 μm, at the most about 80 μm, at the most about 70 μm, at the most about 60 μm, at the most about 50 μm, at the most about 40 μm, at the most about 30 μm, at the most about 20 μm or about 10 μm.

In specific embodiments, the pharmaceutically acceptable sugar alcohol employed has a mean particle size in a range of from about 5 to about 150 μm such as, e.g., from about 5 to about 110 μm or from about 5 to about 80 μm.

Furthermore, it would have been expected that use of e.g. sorbitol in a much smaller particle size would lead to stability problems as it is known that sorbitol is hygroscopic and a smaller particle size increases the surface area and thereby the risk of adsorbing moisture e.g. from the surroundings. However, as demonstrated herein, tablets prepared using a granulate obtained by roller compaction of a composition containing the calcium-containing compound and e.g. sorbitol having a mean particle size well below 300 μm are stable with respect to crushing strength, i.e. the crushing strength of the tablets when stored in open petri dishes at 25° C. and 60% RH changes at the most 50% such as, e.g. at the most about 40%, at the most about 30%, at the most about 20%, at the most about 15%, at the most about 10% during a time period that starts 5 days after manufacture and runs during the remaining storage period e.g. 1 month, 3 months etc. The crushing strengths of tablets of the invention should be in a range of from about 70 to about 140 N.

Such improved stability indicates that products obtained as described herein are suitable for so-called zone 3 or 4 countries (as defined in ICH Q1F), i.e. countries that have a relatively high average temperature and relative humidity.

In one aspect, the invention relates to a process for the preparation of a particulate material or a solid dosage form comprising one or more regularly shaped calcium-containing compound as an active substance and one or more pharmaceutically acceptable sugar alcohols having a micro structure, the process involving roller compaction of a composition containing the calcium-containing compound and the sugar alcohol. The invention also relates to the particulate material as such as well as to a solid dosage form based on the particulate material. The sugar alcohols employed have binding properties and—as in the case of sorbitol and isomalt—preferably sweetening properties.

In order to achieve satisfactory results, the sugar alcohol (binder) must be present in the particulate material in a concentration of at least about 5% w/w such as, e.g., at least about 10% w/w, at least about 15% w/w or at least about 20% w/w.

Use of roller compaction as a means for agglomeration of a calcium-containing compounds to obtain a particulate material that is suitable for use in the preparation of e.g. chewable tablets having an acceptable taste and mouthfeel, has two critical parameters, namely the shape of the calcium carbonate crystals and the structure of the sugar alcohol crystal. Moreover, the pharmaceutically acceptable sugar alcohol (binder) is normally present in a minimum concentration of about 5% w/w or about 10% w/w.

Furthermore, it has been also been observed that when a calcium-containing compound is employed that has a bulk density of at least about 0.7 g/ml (such as e.g. calcium carbonate in the form of Scoralite) then the bulk density of the composition (containing the calcium-containing compound and the sugar alcohol) subjected to roller compaction is not remarkably higher than the bulk density of the calcium-containing compound itself (i.e. before roller compaction). Thus, when such a calcium carbonate quality is used, the bulk density before and after roller compaction may not change much, i.e. the change in bulk density between the particulate material obtained and the calcium-containing compound used is at the most about 40% such as, e.g., at the most about 30% or at the most about 20% calculated as $[(d_{particulate\ material} - d_{calcium-containing\ compound})/d_{particulate\ material}] \times 100\%$.

As mentioned above, the present invention relates to a particulate material comprising one or more regularly shaped calcium-containing compounds as an active substance and one or more pharmaceutically acceptable sugar alcohols having a micro structure. Normally, such a particulate material is further processed into a convenient dosage form such as tablets and such tablets must have suitable technical properties in order to withstand normal handling etc. Furthermore, when chewable tablets are prepared, the tablets must not be so hard, i.e. have an unacceptable high crushing strength, so that it becomes difficult for a patient to chew. Accordingly, it is important to balance the crushing strength to an acceptable level. As shown in the example herein, it is possible to determine whether a specific sugar alcohol is suitable for use in the preparation of a particulate material according to the invention by subjecting the sugar alcohol to two tests, namely i) a SEM photo showing that the sugar alcohol has a micro structure and ii) a test showing the compressibility properties of the sugar alcohol itself. To this end, the pharmaceutically acceptable sugar alcohol—when compressed into tablets containing 100% w/w of the sugar alcohol using 11.29 mm flat faced punches and a max compression force of 25 kN—has a slope of correlation between crushing strength (measured in N) and compression pressure (measured in (N) of $7 \times 10^{-3}$ or more, when tested using a Schleuniger Hardness Autotester 4 or Schleuniger Tablet tester 6D and a tablet placed with the longest dimension orthogonal to the jaws of the crushing strength apparatus.

The inventors have found that it is of great advantage in the roller compaction process to use a pharmaceutically acceptable sugar alcohol that has binding and sweetening properties. Examples of suitable binders or sweeteners include sorbitol, maltitol, xylitol, fructose, lactitol, isomalt, tagatose and manitol. Sorbitol has a sweetening effect (compared to sucrose) of 0.55; maltitol that has a sweetening effect of <1; xylitol that has a sweetening effect of 1, isomalt that has a sweetening effect of <0.5, etc.

In order to ensure a sufficient distribution of the pharmaceutically acceptable sugar alcohol between the individual particles of the calcium-containing compound during the roller compaction, the inventors have found that the binder suitably have a mean particle size of at the most about 110 μm such as, e.g., at the most about 100 μm, at the most about 90 μm, at the most about 80 μm, at the most about 70 μm, at the most about 60 μm, at the most about 50 μm, at the most about 40 μm, at the most about 30 μm, at the most about 20 μm or about 10 μm. Examples of such materials are sorbitol and isomalt.

In the literature (see Pharmaceutical Technology, volume 1 (tabletting technology), Michael H. Rubinstein (ed.), Ellis Horwood Ltd, 1987) it has been stated that sorbitol has good tabletting properties and that the admixing of this excipient will increase the tablet strength. However, it has also been stated that in order to get this effect the sorbitol should be of the "instant" quality that is manufactured by spray-drying. The optimal particle size of sorbitol "instant" has been described as having 60-90% between 212-500 μm when determined by sieve analysis. The recommended concentration in the tablet is 30-80%. However, in the context of the present invention, sorbitol can be used as a binder (having sweetening properties) in tablets based on roller compaction and important deviations from the reported use of sorbitol are necessary:

1. Sorbitol should be finely dispersed or distributed between the particles of the calcium-containing compound in order to secure an optimal or a good as possible binding; this leads to limitations with respect to the particle size of sorbitol.
2. A particle size of sorbitol corresponding to $D_{0.5} < 100$ μm seems to be suitable. The particle size is measured employing Malvern Mastersizer and the size is given as D(v; 0.5).
3. The concentration of sorbitol should exceed that of 5% w/w and approx 20% w/w seems to be fine.
4. Sorbitol of the "instant" quality mentioned above would fail completely if the above described and relatively large particle size distribution was used.

Especially two sugar alcohols have proved to be suitable for use in the roller compaction process, namely sorbitol and isomalt. However, it is contemplated that other sugar alcohols also may be available in a quality that fulfils the above-mentioned criteria, and such sugar alcohols are envisaged to be suitable for use according to the invention. Below is mentioned other sugar alcohols, that may fulfil the above-mentioned criteria.

In a specific embodiment, the sugar alcohol is sorbitol, notable a sorbitol that has a mean particle size in a range of from about 25 to about 50 μm such as, e.g., from about 35 to about 45 μm or from about 30 to about 45 μm.

In another embodiment, the sugar alcohol is isomalt, notably an isomalt that has a mean particle size in a range of from about 20 to about 50 μm such as, e.g., from about 25 to about 35 μm or from about 20 to about 35 μm.

Provided that a sugar alcohol is employed that fulfils the above-mentioned criteria it is possible to use one or more sugar alcohols that not necessarily fulfils these criteria, but has other functions e.g. as a sweetener. Such sugar alcohols are typically selected from the group consisting of mannitol, xylitol, maltitol, inositol, and lactitol, and mixtures thereof. Examples are Sorbitols, Neosorb P100T, Sorbidex P1666B0 and Sorbogem Fines Crystalline Sorbitol available from Roquette Freres, Cerestar and SPI Polyols Inc. respectively. Maltisorb P90 (maltitol) available from Roquette Freres, Xylitol CM50, Fructofin CM (fructose) and Lactitol CM50 available from Danisco Sweeteners, Isomalt ST-PF, Isomalt DC100, Gaio Tagatose and Manitol available from Palatinit, Arla Foods and Roquette, Freres respectively. Further examples of suitable saccharide-based binders/sweeteners include sucrose, dextrose. Specific qualities of sorbitol and isomalt that do not fulfil the above-mentioned criteria may of course also be added.

In a specific embodiment, a particulate material according to the invention may comprise a mixture of sorbitol and xylitol. In such cases, the weight ratio between sorbitol and xylitol is normally in a range of from about 1:0.1 to about 1:1.5 such as, e.g., about 1:1. A mixture of isomalt and xylitol is also suitable and in such cases, the weight ratio between isomalt and xylitol is normally in a range of from about 1:0.1 to about 1:1.5 such as, e.g., about 1:1.

In a paragraph given in the following, a description of calcium-containing compounds is given. However, as mentioned herein before, the calcium-containing compound for use in the roller compaction process according to the invention has a regular shape such as a calcium salt like calcium carbonate in specific qualities. In preferred aspect, the calcium salt is calcium carbonate and notably with a shape and a mean particle size corresponding to that of Scoralite 1B or Merck 2064. In a specific embodiment, the calcium carbonate is Scoralite 1B or Merck 2064.

However, the above-mentioned calcium carbonate may be used in admixture with other calcium-containing compounds such as, e.g., those mentioned herein in the following paragraph, especially calcium citrate, calcium lactate, calcium phosphate including tricalcium phosphate, calcium gluconate, bisglycino calcium, calcium citrate maleate, hydroxyapatite including solvates, and mixtures thereof.

Normally, the content of the regularly shaped calcium-containing compound in the particulate material is in a range of from about 40% to about 100% w/w such as, e.g., from about 45% to about 98% w/w, from about 50% to about 95% w/w, from about 55% to about 90% w/w or at least about 60% w/w, at least about 65% w/w, at least about 70% w/w or at least about 75% w/w.

The particulate material obtained by roller compaction may comprise 100% w/w of the calcium-containing compound or it may comprise from about 50% to about 90% w/w such as, e.g., from about 70 to about 80% w/w of the total amount of calcium-containing compound contained in the tablet. Accordingly, a part of the total amount of calcium-containing compound may be added after roller compaction.

As mentioned above, during the roller compaction process, the calcium carbonate and the sugar alcohol are brought in close contact and due to the micro structure of the crystal of the sugar alcohol, the sugar alcohol crystals are squeezed between the calcium carbonate crystal. Accordingly, a SEM photo of the particulate material—when compressed into a tablet—shows that a surface of a deformed particle of the pharmaceutically acceptable sugar alcohol is in close contact with surfaces of the crystals of the one or more calcium-containing compound.

A particulate material according to the invention may further comprise one or more pharmaceutically acceptable excipients or additives, or one or more therapeutically, prophylactically and/or diagnostically active substances. A description of pharmaceutically acceptable excipients suitable for use in the present context is given herein.

A particular active substance of interest is a vitamin D.

Furthermore, roller compaction of a composition containing a calcium-containing compound and a sugar alcohol to obtain a particulate material according to the invention leads to a particulate material that has such a flowability that—when tablets are prepared from the particulate material optionally admixed with at the most 10% w/w such as, e.g. at the most about 7.5% w/w or at the most about 5% w/w of a glidant using a tabletting machine operating at least 300 tablets per min—the mass variation of the tablets obtained fulfils the requirements given in Ph. Eur. The tabletting machine may be operating at e.g. 1000 tablets/min or even higher such as, e.g., 2000 tablets/min, 3000 tablets/min, 4000 tablets/min, 5000 tablets/min, 6500 tablets/min etc. The dwell time during the preparation of the tablets is at the most about 1 sec.

In a specific embodiment a particulate material according to the invention contains from about 60 to about 95% w/w of the calcium-containing compound and from about 5 to about 40% w/w of the pharmaceutically acceptable sugar alcohol, provided that the sum does not exceed 100% w/w.

In another specific embodiment a particulate material according to the invention contains from about 60 to about 94% w/w such as, e.g., from about 65% to about 80% w/w of the calcium-containing compound, from about 5 to about 35% w/w such as, e.g., from about 15 to about 30% w/w of the pharmaceutically acceptable sugar alcohol and from about 1 to about 15% w/w of one or more pharmaceutically acceptable excipients and/or active substances, provided that the sum of ingredients amounts to 100% w/w.

More specifically, a particulate material according to the invention preferably contains from about 65% to about 80% w/w such as, e.g., from about 70% to about 75% w/w of the calcium-containing compound and from about 15% to about 25% w/w such as, e.g., from about 20 to about 25% w/w of sorbitol or isomalt or mixtures thereof.

A particulate material according to the invention may be used as such, but normally it is manufactured into a suitable solid dosage form. One or more pharmaceutically acceptable excipients may be added in order to prepare the dosage form. The dosage form is intended for oral administration e.g. in the form of a single unit or a multiple unit dosage form such as, e.g., in the form of tablets, capsules, sachets, beads, pellets or the like.

In a preferred embodiment, the solid dosage form according to the invention is in the form of tablets.

In a specific embodiment the tablets have a shape and dimensions essentially as shown in FIG. 24 herein. This shape is especially designed to easily break the tablet into two halves of essentially the same size, i.e. essentially containing the same amount of calcium. The breakage is provided by placing the tablet on a flat surface e.g. a table and then by use of e.g. two fingers pressing simultaneously on each end of the tablet. Due to the fact that the tablet is in contact with the table only in one point this is possible.

A solid dosage form according to the invention may contain an amount of the one or more calcium-containing compounds corresponding to from about 300 to about 1200 mg calcium such as, e.g., from about 400 to about 600 mg calcium. Normally, the total concentration of the one or more calcium-containing compound in the dosage form is in a range of from about 40% to about 99% w/w such as, e.g., from about 45% to about 98% w/w, from about 50% to about 95% w/w, from about 55% to about 90% w/w or at least about 60% w/w, at least about 65% w/w, at least about 70% w/w.

In a specific embodiment, the total concentration of the particulate material contained in the dosage form is from about 65% to about 100% w/w such as, e.g., from about 70% to about 98% w/w, from about 75% to about 95% w/w, from about 80% to about 95% or from about 85% to about 95% w/w.

In another specific embodiment, a solid dosage form according to the invention contains from about 60% to about 95% w/w of the calcium-containing compound and from about 5% to about 40% w/w of the pharmaceutically acceptable sugar alcohol, provided that the sum does not exceed 100% w/w. Alternatively, a solid dosage form contains from about 60 to about 94% w/w such as, e.g., from about 65% to about 80% w/w of the calcium-containing compound, from about 5 to about 35% w/w such as, e.g., from about 15 to about 30% w/w of the pharmaceutically acceptable sugar alcohol and from about 1 to about 15% w/w of one or more pharmaceutically acceptable excipients and/or active substances, provided that the sum of ingredients amounts to 100% w/w.

A SEM photo of a fractured surface of the solid dosage form shows that a surface of a deformed particle of sugar alcohol is in close contact with surfaces of the one or more calcium-containing compound.

As mentioned herein before, a solid dosage form according to the invention is stable. Accordingly, the crushing strength of the tablets when stored in open petri dishes at 25° C. and 60% RH at the most changes 50% such as, e.g. at the most about 40%, at the most about 30%, at the most about 20%, at the most about 15%, at the most about 10% during a time period that starts 5 days after manufacture and runs during the remaining storage period. Acceptable stability is obtained if a tablet during the whole storage period (e.g. 1 month, 3 months) in open Petri dishes has a crushing strength in a range of from about 70 to about 140 N.

In a preferred aspect, a solid dosage form is in the form of a chewable, suckable and/or swallowable tablet. Importantly for chewable tablets is the taste and such tablets of the invention must have an acceptable taste with respect to sweetness, flavour and chalkiness when tested by a professional/skilled sensory test panel of at least 6 persons.

A solid dosage form according to the invention may comprise a sweetener selected from the group consisting of dextrose, fructose, glycerin, glucose, isomalt, lactitol, lactose, maltitol, maltose, mannitol, sorbitol, sucrose, tagatose, trehalose, xylitol, alitame, aspartame, acesulfam potassium, cyclamic acid, cyclamate salt (e.g. calcium cyclamate, sodium cyclamate), neohesperidine dihydrochalcone, thaumatin, saccharin, saccharin salt (e.g. ammonium saccharin, calcium saccharin, potassium saccharin, sodium saccharin), and mixtures thereof.

The invention also relates to a process for the preparation of a particulate material as defined above, the process comprises roller compaction of a composition comprising the regularly shaped calcium-containing compound and one or more pharmaceutically acceptable sugar alcohols having a micro structure. Details concerning this aspect appear from the appended claims and from the description above relating to the particulate material apply mutatis mutandis to this and other aspects of the invention.

A further aspect of the invention is to combine the manufacture of a particulate material and the manufacture of tablets. By use of pocket rollers on the roller compactor a powder mixture can be transformed directly into a solid dosage form, that is a tablet.

A further aspect of the invention is a process for preparing a tablet comprising a calcium-containing compound, the process comprises
i) preparing a particulate material as defined herein,
ii) optionally admixing one or more pharmaceutically acceptable excipients or additive and/or one or more active substances, and
iii) compressing the material into tablets.

Normally, the compression in step iii) is performed at a compression force that is adjusted with respect to the diameter and the desired height of the tablet so that the compression force applied is at the most about 80 kN such as, e.g., at the most 70 kN, at the most 60 kN, at the most 50 kN, at the most about 40 kN, at the most about 30 kN or at the most about 20 kN when tablets having a diameter of about 16 mm or is capsule shaped (9.4×18.9 mm) and a resulting height of at the most about 10 mm such as, e.g., about 9 mm, about 8 mm or about 7 mm or about 6 mm are obtained.

Specifically, the invention relates to a process according for the preparation of a tablet comprising
i) calcium carbonate
ii) sorbitol and/or isomalt,
iii) a vitamin D, and
iv) optionally one or more pharmaceutically acceptable excipients.

The tablet may comprise
i) from about 50% to about 90% w/w of calcium carbonate,
ii) from about 5 to about 30% w/w of sorbitol and/or isomalt,
iii) from about 0.01 to about 1% w/w of a vitamin D, and
iv) optionally one or more pharmaceutically acceptable excipients
with the proviso that the total amount of ingredients corresponds to about 100% w/w.

Calcium-containing Compound

The calcium-containing compound contained in a particulate material made according to the invention is a physiologically tolerable calcium-containing compound that is therapeutically and/or prophylactically active.

Calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellular calcium levels (Burgoyne R D. Biochim Biophys Acta 1984; 779: 201-16). The secretion of hormones and the activity of key enzymes and proteins are dependent on calcium. Finally calcium as a calcium phosphate complex confers rigidity and strength on the skeleton (Boskey A L. Springer, 1988: 171-26). Because bone contains over 99% of the total body calcium, skeletal calcium also serves as the major long-term calcium reservoir.

Calcium salts such as, e.g., calcium carbonate is used as a source of calcium especially for patients suffering from or at risk of osteoporosis. Moreover, calcium carbonate is used as an acid-neutralizing agent in antacid tablets.

As mentioned above, calcium has a number of important functions within the mammalian body in particular in humans. Furthermore, in many animal models, chronic low calcium intake produces osteopenia. The osteopenia affects cancellous bone more than cortical bone and may not be completely reversible with calcium supplementation. If the animal is growing reduced calcium intake leads to stunting. In the premature human neonate the higher the calcium intake, the greater the increase in skeletal calcium accretion which, if high enough, can equal gestational calcium retention. During growth chronic calcium deficiency causes rickets. Calcium supplements in both pre- and postpubertal healthy children leads to increased bone mass. In adolescents the higher the calcium intake, the greater the calcium retention, with the highest retention occurring just after menarche. Taken together, these data suggest that in children and adolescents considered to be taking an adequate intake of calcium, peak bone mass can be optimized by supplementing the diet with calcium. The mechanisms involved in optimizing deposition of calcium in the skeleton during growth are unknown. They are probably innate properties of the mineralization process that ensures optimal calcification of the osteoid if calcium supplies are high. The factors responsible for stunting of growth in states of calcium deficiency are also unknown but clearly involve growth factors regulating skeletal size.

In adults calcium supplementation reduces the rate of age-related bone loss (Dawson-Hughes B. Am J Clin Nut 1991; 54:S274-80). Calcium supplements are important for individuals who cannot or will nor achieve optimal calcium intakes from food. Furthermore, calcium supplement is important in the prevention and treatment of osteoporosis etc.

Furthermore, calcium may have anticancer actions within the colon. Several preliminary studies have shown high calcium diets or intake of calcium supplementation is associated with reduced colon rectal cancer. There is increasing evidence that calcium in combination with acetylsalicylic acid (ASA) and other non-steroidal anti-inflammatory drugs (NSAIDS) reduce the risk the risk of colorectal cancer.

Recent research studies suggest that calcium might relieve premenstrual syndrome (PMS). Some researchers believe that disruptions in calcium regulation are an underlying factor in the development of PMS symptoms. In one study, half the women of a 466 person group of pre-menopausal women from across the U.S. were tracked for three menstrual cycles and were given 1200 mg of calcium supplements daily throughout the cycle. The final results showed that 48% of the women who took placebo had PMS related symptoms. Only 30% of those receiving calcium tablets did.

Calcium salts like e.g. calcium carbonate is used in tablets and due to the high dose of calcium required, such tablets are often in the form of chewable tablets. It is a challenge to formulate e.g. chewable tablets containing a calcium salt, which tablets have a pleasant taste and an acceptable mouth feel without the characteristic dominating taste or feeling of chalk.

A calcium-containing compound for use according to the invention may be e.g. bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Other calcium sources may be water-soluble calcium salts, or complexes like e.g. calcium alginate, calcium-EDTA and the like or organic compounds containing calcium like e.g. calcium organophosphates. Use of bone meal, dolomite and other unrefined calcium sources is discouraged because these sources may contain lead and other toxic contaminants. However, such sources may be relevant if they are purified to a desired degree.

The calcium-containing compound may be used alone or in combination with other calcium-containing compounds.

Of specific interest is bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Mixtures of different calcium-containing compounds may also be used. As appears from the examples herein, calcium carbonate is especially suitable for use as a calcium-containing compound and calcium carbonate has a high content of calcium.

Of particular interest is calcium carbonate.

Normally, a tablet made according to the invention contains an amount of the calcium-containing compound corresponding to from about 100 to about 1000 mg Ca such as, e.g., from about 150 to about 800 mg, from about 200 to about 700 mg, from about 200 to about 600 mg or from about 200 to about 500 mg Ca.

Calcium Carbonate

Calcium carbonate can be in three different crystal structures: calcite, aragonite and vaterite. Mineralogically, these are specific mineral phases, which relate to the distinct arrangement of the calcium, carbon and oxygen atoms in the crystal structure. These distinct phases influence the shape and symmetry of the crystal forms. For example, calcite is available in four different shapes: scalenohedral, prismatic, spherical and rhombohedral, and aragonit crystals can be obtained as e.g. discrete or clustered needle-like shapes. Other shapes are also available such as, e.g., cubic shapes (Scoralite 1A+B from Scora).

As shown in the examples herein, a particular suitable quality of calcium carbonate is calcium carbonate having a mean particle size of 60 μm or less such as, e.g., 50 μm or less or 40 μm or less.

Furthermore, an interesting quality of calcium carbonate has a bulk density below 2 g/mL.

Calcium carbonate 2064 Merck (available from Merck, Darmstadt, Germany) that has a mean particle size of 10-30 μm, an apparent bulk density of 0.4 to 0.7 g/mL, and a specific surface area of 0.3 $m^2/g$;

Calcium carbonate 2069 Merck (available from Merck, Darmstadt, Germany) that has a mean particle size of approx. 3.9 μm, and an apparent bulk density of 0.4 to 0.7 g/mL;

Scoralite 1A (available from Scora Watrigant SA, France) has a mean particle size of 5 to 20 μm, an apparent bulk density of 0.7 to 1.0 g/mL, and a specific surface area of 0.6 $m^2/g$;

Scoralite 1B (available from Scora Watrigant SA, France) has a mean particle size of 10-25 μm, an apparent bulk density of 0.9 to 1.2 g/mL, and a specific surface area of 0.4 to 0.6 $m^2/g$;

Scoralite 1A+B (available from Scora Watrigant SA, France) have a mean particle size of 7-25 μm, an apparent bulk density of 0.7 to 1.2 g/mL, and a specific surface area of 0.35 to 0.8 $m^2/g$;

Pharmacarb LL (available from Chr. Hansen, Mahawah N.J.) L has a mean particle size of 12-16 μm, an apparent bulk density of 1.0 to 1.5 g/mL, and a specific surface area of 0.7 $m^2/g$;

Sturcal H has a mean particle size of approx. 4 μm, an apparent bulk density of 0.48 to 0.61 g/mL;

Sturcal F has a mean particle size of approx. 2.5 μm, an apparent bulk density of 0.32 to 0.43 g/mL;

Sturcal M has a mean particle size of 7 μm, an apparent bulk density of 0.7 to 1.0 g/mL, and a specific surface area of 1.0 $m^2/g$;

Mikhart 10, SPL, 15, 40 and 65 (available from Provencale, Provencale, France);

Mikhart 10 has a mean particle size of 10 μm,

Mikhart SPL has a mean particle size of 20 μm,

Mikhart 15 has a mean particle size of 17 μm,

Mikhart 40 has a mean particle size of 30 μm, an apparent bulk density of 1.1 to 1.5 g/mL;

Mikhart 65 has a mean particle size of 60 μm, an apparent bulk density of 1.25 to 1.7 g/mL;

Omyapure 35, (available from Omya S.A.S, Paris, France) has a mean particle size of 5-30 μm, and a specific surface area of 2.9 $m^2/g$;

Socal P2PHV (available from Solvay, Brussels, Belgium) has a mean particle size of 1.5 µm, an apparent bulk density of 0.28 g/mL, and a specific surface area of 7.0 m$^2$/g;

Calci Pure 250 Heavy, Calci Pure 250 Extra Heavy and Calci Pure GCC HD 212 with a mean particle size of 10-30 µm, an apparent bulk density of 0.9-1.2 g/ml, and a specific surface area of 0.7 m$^2$/g (available from Particle Dynamic Inc., St. Louis Mont.).

The content of the calcium-containing compound in a tablet made according to the present invention is in a range from about 40% to about 100% w/w such as, e.g., from about 45% to about 98% w/w, from about 50% to about 95% w/w, from about 55% to about 90% w/w or at least about 60% w/w, at least about 65% w/w, at least about 70% w/w or at least about 75% w/w.

Normally, the dose of calcium for therapeutic or prophylactic purposes is from about 350 mg (e.g. newborn) to about 1200 mg (lactating women) daily. The amount of the calcium-containing compound in the tablets can be adjusted to that the tablets are suitable for administration 1-4 times daily, preferably once or twice daily.

As mentioned above, the granulate obtained by the method according to the invention may be used as such, but it is also very suitable for further manufacturing into solid dosage forms like e.g. tablets, capsules or sachets.

A person skilled in the art will know how to adjust the composition and the various process parameters in order to obtain a desired calcium-containing product.

In one embodiment of the invention, the granulate obtained by the present method is intended to be manufactured into tablets. Often it is necessary to add one or more pharmaceutically acceptable excipients (e.g. lubricants) in order to avoid adherence and/or increase flowability of the granulate obtained. Accordingly, the method may also comprise a step of mixing the granulate obtained with one or more pharmaceutically acceptable excipients.

In the event that it is desired to include other active substances than the calcium-containing compound, the method may also comprise a step of adding one or more therapeutically, prophylactically and/or diagnostically active substance to the granulate obtained.

Such substances include one or more nutrients such as, e.g., one or more vitamins or minerals. In a specific embodiment, the further active substance is a D-vitamin such as, e.g., D$_3$ vitamin, D$_2$ vitamin or derivatives thereof.

D Vitamin or Other Active Substances

A particulate material as well as a tablet obtained according to the invention may comprise a further therapeutically and/or prophylactically active substance. Of particular interest are one or more D-vitamin compounds. Non-limiting examples are dry vitamin D3, 100 CWS available from Roche and dry vitamin D3 100 GFP available from BASF.

A particulate material or tablet made according to the invention may comprise a further therapeutically and/or prophylactically active substance, or it may contain one or more nutrients such as, e.g. one or more vitamins or minerals. Of specific interest are e.g. vitamin B, vitamin C, vitamin D and/or vitamin K and minerals like e.g. zinc, magnesium, selenium etc.

Of particular interest are one or more D-vitamin compounds such as, e.g., Vitamin D$_2$ (ergocalciferol) and Vitamin D$_3$ (cholecalciferol) including dry vitamin D$_3$, 100 CWS available from Roche and dry vitamin D$_3$100 GFP available from BASF.

In addition to its action on calcium and skeletal homeostasis, vitamin D is involved in the regulation of several major systems in the body. The actions of vitamin D are medicated at the genome by a complex formed by 1,25-(OH)$_2$ vitamin D mainly produced in the kidney, with the vitamin D receptor (VDR). The latter is widely distributed in many cell types. The 1,25-(OH)$_2$ vitamin D/VDR complex has important regulatory roles in cell differentiation and in the immune system. Some of these actions are probably dependant on the ability of certain tissues other than the kidney to produce 1,25-(OH)$_2$ vitamin D locally and act as a paracrine (Adams J S et al. Endocrinology 1996; 137: 4514-7).

In humans, deficiency of vitamin D results in rickets in children and osteomalacia in adults. The basic abnormality is a delay in the rate of mineralization off osteoid as it is laid down by the osteoblast (Peacock M. London Livingstone, 1993:83-118). It is not clear whether this delay is due to a failure of a 1,25-(OH)$_2$ vitamin D-dependant mechanism in the osteoblast or to reduced supplies of calcium and phosphate secondary to malabsorption or a combination of both. Accompanying the mineralization delay, there is reduced supply of calcium and phosphate, severe secondary hyperparathyroidism with hypocalcaemia and hypophosphatemia and increased bone turnover.

Vitamin D insufficiency, the preclinical phase of vitamin D deficiency, also causes a reduced calcium supply and secondary hyperparathyroidism, albeit of a milder degree than found with deficiency. If this state remains chronic, osteopenia results. The biochemical process underlying this state of calcium insufficiency is probably inappropriate level of 1,25-(OH)$_2$ vitamin D due to a reduction in its substrate 25-OHD (Francis R M et al. Eur J Clin Invest 1983; 13:391-6). The state of vitamin D insufficiency is most commonly found in the elderly. With age there is a decrease in serum 25-OH vitamin D due to decreased sunlight exposure and possible to decreased skin synthesis. Furthermore, in the elderly the condition is exacerbated by a decrease in calcium intake and a paradoxical decrease in calcium absorption. The reduction in renal function with age giving rise to reduced renal 1,25-(OH)$_2$ vitamin D production may be a contributing factor. There are a number of studies of the effects of vitamin D supplementation on bone loss in the elderly. Some are without calcium supplementation and others are with calcium supplementation. It appears from the studies that although vitamin D supplementation is necessary to reverse deficiency and insufficiency, it is even more important as far as the skeleton is concerned to provide calcium supplementation since the major skeletal defect is calcium deficiency. In literature based on clinical trials, recent findings suggest trends of need for higher doses of vitamin D for the elderly patients (Compston J E. BMJ 1998; 317:1466-67). An open quasi-randomised study of annual injections of 150.000-300.000 IU of vitamin D (corresponding to approx. 400-800 IU/day) showed a significant reduction in overall fracture rate but not in the rate of hip fracture in treated patients (Heikinheimo R J et al. Calcif Tissue Int 1992; 51:105-110).

As it appears from above, a combination of calcium and vitamin D is of interest. The recommended Daily Allowance (RDA) of calcium and vitamin D$_3$ are as follows (European Commission. Report on osteoporosis in the European Community. Action for prevention. Office for official Publications of the European Communities, Luxembourg 1998):

| Group | Age (years) | Calcium (mg)* | Vitamin D$_3$ (µg) |
|---|---|---|---|
| Newborn | 0-0.5 | 400 | 10-25 |
| | 0.5-1.0 | 360-400 | 10-25 |

| Group | Age (years) | Calcium (mg)* | Vitamin D₃ (μg) |
|---|---|---|---|
| Children | 1.0-3.0 | 400-600 | 10 |
| | 4.0-7.0 | 450-600 | 0-10 |
| | 8.0-10 | 550-700 | 0-10 |
| Men | 11-17 | 900-1000 | 0-10 |
| | 18-24 | 900-1000 | 0-15 |
| | 25-65 | 700-800 | 0-10 |
| | 65+ | 700-800 | 10 |
| Women | 11-17 | 900-1000 | 0-15 |
| | 18-24 | 900-1000 | 0-10 |
| | 25-50 | 700-800 | 0-10 |
| | 51-65 | 800 | 0-10 |
| | 65+ | 700-800 | 10 |
| Pregnant | | 700-900 | 10 |
| Lactating | | 1200 | 10 |

*RDA of calcium varies from country to country and is being re-evaluated in many countries.

Vitamin D is very sensitive towards humidity and is subject to degradation. Therefore, vitamin D is often administered in a protective matrix. Accordingly, when tablets are prepared containing a vitamin D it is of utmost importance that the compression forces applied during the tabletting step do not decrease the protective effect of the matrix and thereby impair the stability of vitamin D. To this end, the combination of the various ingredients in a granulate or tablet made according to the invention has proved to be very suitable in those cases where vitamin D also is incorporated into the composition as it is possible to employ a relatively low compression force during tabletting and still achieve a tablet with suitable mechanical strength (crushing strength, friability etc.).

As indicated above, a tablet containing vitamin D is contemplated to fulfil the following requirements with respect to stability:

After storage in a closed container at 25° C. at 60% relative humidity (RH) for at least 6 month such as, e.g., at least 1 year, at least 1.5 years, at least 2 years or at least 5 years, there is a decrease in the content of D vitamin of at the most about 15% w/w such as, e.g., at the most about 10% w/w or at the most about 5% w/w.

After storage in a closed container at 40° C. at 75% relative humidity (RH) for at least 1 month such as, e.g., at least 2 months, at least 4 months or at least 6 months, there is a decrease in the content of D vitamin of at the most about 15% w/w such as, e.g., at the most about 10% w/w or at the most about 5% w/w.

In a specific embodiment, the invention provides a tablet comprising
i) a calcium-containing compound as an active substance,
ii) a vitamin D, and
iii) optionally one or more pharmaceutically acceptable excipients or actives.

More specifically, the tablet may comprise
i) at least 200 mg of the calcium-containing compound (normal range 200-1500 mg),
ii) at least 5 μg of vitamin D (normal range 5-100 μg-1 μg=40 IU), and
iii) optionally one or more pharmaceutically acceptable excipients or actives.

In a specific embodiment, the invention provides a tablet comprising
i) from about 50% to about 90% w/w of the calcium-containing compound,
ii) from about 0.00029% to about 0.0122% w/w of a vitamin D, and
iii) optionally one or more pharmaceutically acceptable excipients or actives
with the proviso that the total amount of ingredients corresponds to about 100% w/w.

In particular, the tablet may comprise
i) from about 50% to about 90% w/w of the calcium-containing compound,
ii) from about 5 to about 40% w/w of a sweetening agent,
iii) from about 0.12% to about 4.9% w/w of a vitamin D including a protective matrix,
iv) optionally one or more pharmaceutically acceptable excipients or actives
with the proviso that the total amount of ingredients corresponds to about 100% w/w.

Pharmaceutically Acceptable Excipients

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties. Although a pharmaceutically acceptable excipient may have some influence on the release of the active drug substance, materials useful for obtaining modified release are not included in this definition.

The calcium-containing compound and the sugar alcohol may also be admixed with one or more pharmaceutically acceptable excipients before or after roller compaction. Such excipients include those normally used in formulation of solid dosage forms such as, e.g. fillers, binders, disintegrants, lubricants, flavouring agents, colouring agents, including sweeteners, pH adjusting agents, stabilizing agents, etc.

Typically, a disintegrant is selected from the group consisting of: croscarmellose sodium (a cross-linked polymer of carboxymethylcellulose sodium), crospovidone, starch NF; polacrilin sodium or potassium and sodium starch glycolate. Those skilled in the art will appreciate that it is desirable for compressible tablets to disintegrate within 30 minutes, more desirable within 10 min, most desirable within 5 min; therefore, the disintegrant used preferably results in the disintegration of the tablet within 30 minutes, more preferable within 10 min, most preferable within 5 min.

Examples of disintegrants that may be used are e.g. cellulose derivatives, including microcrystalline cellulose, low-substituted hydroxypropyl cellulose (e.g. LH 22, LH 21, LH 20, LH 32, LH 31, LH30); starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel® and Explotab®).

Fillers/diluents/binders may be incorporated such as polyols, sucrose, sorbitol, mannitol, Erythritol®, Tagatose®, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-HPC-CH31, L-HPC-LH11, LH 22, LH 21, LH 20, LH 32, LH 31, LH30), dextrins, maltodextrins (e.g. Lodex® 5 and Lodex® 10), starches or modified starches (including potato starch, maize starch and rice starch), sodium chloride, sodium phosphate, calcium sulfate, calcium carbonate.

In pharmaceutical compositions made according to the present invention, especially microcrystalline cellulose, L-hydroxypropylcellulose, dextrins, maltodextrins, starches and modified starches have proved to be well suited.

In a specific embodiment of the invention, the calcium-containing compound may be roller compacted together with one or more pharmaceutically acceptable binders, or a binder may be added after roller compaction. Suitable binders include those normally used within the pharmaceutical field although binders usually employed in wet granulation processes are not likely to be able to function to the same extent as essentially no liquid is present in during the agglomeration.

More specifically, examples include
cellulose derivates including methylcellulose, hydroxypropylcellulose (HPC, L-HPC), hydroxypropylmethylcellulose (HPMC), microcrystalline cellulose (MCC), sodium carboxymethylcellulose (Na-CMC), etc.;
mono- di-, oligo-, polysaccharides including dextrose, fructose, glucose, isomalt, lactose, maltose, sucrose, tagatose, trehalose, inulin and maltodextrin;
polyols including sugar alcohols such as, e.g., lactitol, maltitol, mannitol, sorbitol, xylitol and inositol;
polyvinylpyrrolidone including Kollidon K30, Kollidon 90F or Kollidon VA64 and
proteins including casein.

Glidants and lubricants may be incorporated such as stearic acid, metallic stearates, talc, waxes and glycerides with high melting temperatures, colloidal silica, sodium stearyl fumarate, polyethylenglycols and alkyl sulphates.

Surfactants may be employed such as non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitane monoisostearate, sorbitanmonolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate) and cationic (e.g., benzalkonium chloride, benzethonium chloride and cetrimide) or mixtures thereof.

Other appropriate pharmaceutically acceptable excipients may include colorants, flavouring agents, and buffering agents.

As appears from the claims, the present invention also provides a method comprising the step of processing the particulate material obtained by roller compaction into a solid dosage form. Such dosage forms may be provided with a coating provided that the coating does not substantially retard the release of the active drug substance from the composition. Typically, a film coating may be employed.

Suitable lubricants include talc, magnesium stearate, calcium stearate, stearic acid, hydrogenated vegetable oils and the like. Preferably, magnesium stearate is used.

Suitable bulking agents include xylitol, mannitol, compressible sugars, lactose, calcium phosphate and microcrystalline celluloses.

Suitable artificial sweeteners include dextrose, fructose, glycerin, glucose, isomalt, lactitol, lactose, maltitol, maltose, mannitol, sorbitol, sucrose, tagatose, trehalose, xylitol, alitame, aspartame, acesulfam potassium, cyclamic acid, cyclamate salt (e.g. calcium cyclamate, sodium cyclamate), neohesperidine dihydrochalcone, thaumatin, saccharin, saccharin salt (e.g. ammonium saccharin, calcium saccharin, potassium saccharin, sodium saccharin), and mixtures thereof.

If desired known flavourants and known FD & C colorants can be added to the composition.

Specific Aspect Relating to Tablets Designed for Dose Dispensing Machines

In today's world the global healthcare area faces major changes. The future holds further medical advancement with an increasing elderly population demanding extended care. To improve compliance for e.g. the elderly population, packing of medicine in daily unit/multiple dose packages ("dose dispensing") is implemented in more and more countries such as, e.g., European countries. Typically the medicine is dosed for a two weeks period of time and the daily dose package contains e.g. packages/bags for the morning, noon, evening and night medication. On each bag information about the person and the medicine are printed.

Development of tablets that are sufficiently robust to be dispensed via a dose-dispensing machine is a particular challenge when the tablets are formulated as chewable tablets. Normally, chewable tablets do not have sufficient technical properties, which are required for a dose-dispensing machine (e.g. the tablets are too fragile and when exposed to the filling equipment they afford dust which makes the filling difficult or impossible). Today no product is available on the market containing a calcium-containing compound as a therapeutically and/or prophylactically active substance and being chewable, i.e. having an acceptable taste and mouthfeel, and at the same time having sufficient technical properties to enable dispensing via a dose-dispensing machine. Accordingly, it is not possible for patients to obtain a daily dose package packed by a dose-dispensing machine, which package includes one or more calcium-containing chewable tablets. The present inventors address this issue by providing a tablet that is sufficient robust to withstand packaging by a dose-dispensing machine and at the same time gives the patient or the user the liberty of choosing whether she wants to chew, suck and/or swallow the tablet, i.e. the improved technical properties do not impair an acceptable taste and mouthfeel.

As appears from the above, the present invention solves the problem of providing chewing tablets with an acceptable taste (which tablets also may be sucked or swallowed) and with mechanical properties and a size that are suitable for use when the tablets are dispensed by a dose-dispensing machine.

In general, improved outcomes and reduced costs are some of the advantages in applying a dose-dispensing machine, which may be achieved by, e.g.,
i) reduced distribution time, which increases staff efficiency and releases staff to other functions,
ii) reduced incidence of prescribing, dispensing and/or administration errors,
iii) improved patient care by clearly labelled unit/multi dose packages, which help patients receiving the right medication at the right time, and/or
iv) reduced waste of medicine.

As mentioned above, the regulatory requirements for tablets dispensed by a dose-dispensing machine are relative high, and they may be different from country to country with regard to the application, type of medicine, stability etc.

Currently, there are three important types of dose-dispensing machines on the market, namely a Tosho machine type Main-Topra 2441 CE. This machine doses in small plastic bags and doses up to 244 different compositions. Another type Main-Topra 4001 CE doses up to 400 different compositions with the same speed as Main-Topra 2441 CE (45 bags/min).

Automed Technologies Inc, USA, has e.g. the type ATC 212 on the European market. This machine doses in small plastic bags and doses up to 212 different compositions. The machine packs 25 bags/min. Other recent types are improved with respect to number of different compositions to be packed (330 or 520) and the speed is increased to 60 bags/min.

Hyupshin Medical co. Ltd has a dose-dispensing machine, ATDPS, which doses in small plastic bags and doses up to 352 different compositions. The speed is 60 bags/min. Furthermore, new machines have been developed (ATDPS JV-500SL and ATDPS JV-352SL), which doses up to 500 different compositions with the same speed (60 bags/min).

Due to the different size and shapes of tablets and capsules, the machines are supplied with different types of cassettes and rotary parts, which ensure that only one tablet or capsule is dosed at the same time. The main body of the cassettes is well shielded from light, it is dust-tight and damp-proof, so the cassettes are well-suited to store the medicine. Misplacing the cassettes is not possible because of a safety lock. Tablets and capsules will not be stored in the cassettes for more than a defined period of time to ensure the quality of the compositions. The machines will make a notice when a composition has been stored in the cassettes for more than this period of time.

With respect to the size of the tablets, the following requirements should be met in order to ensure that the tablets can be packed with a dose-dispensing machine: The requirements are dynamic and may change over time.

| Dimension of Round Tablet | | | |
|---|---|---|---|
| Distributor | Interval | Length (mm) | Thickness (mm) |
| Tosho | Minimum | | |
| | Maximum | 14.0 | 9.4 |
| Hyupshin | Minimum | 5.5 | 1.5 |
| | Maximum | 13.2 | 6.7 |
| Automed Tech. | Minimum | 4.6 | 2.2 |
| | Maximum | 14.0 | 7.0 |

| Dimension of Oval Tablet | | | | |
|---|---|---|---|---|
| Distributor | Interval | Length (mm) | Thickness (mm) | Width (mm) |
| Tosho | Minimum | | | |
| | Maximum | 21.5 | 7.5 | 7.5 |
| Hyupshin | Minimum | 8.5 | 2.7 | 4.0 |
| | Maximum | 20.0 | 7.7 | 10.0 |
| Automed Tech. | Minimum | 6.9 | 2.2 | 4.6 |
| | Maximum | 21.0 | 7.5 | 11.7 |

The above-mentioned dimension for a round or an oval tablet may be changed and still fit into the specified dose-dispensing machine. Experiments performed by the present inventors have shown that a variation in a range of ±20% is acceptable, preferable ±10%. With respect to the size, one of the major problems, the inventors were faced with was to reduce the thickness of the tablets. This was solved by using a proper combination of active ingredient(s) and pharmaceutically acceptable excipients and by a careful selection of a suitable particle size and/or crystal form of the calcium-containing compound, the properties of the excipients and the preparation method.

It is of importance that the tablets do not create dust and as mentioned above, the tablets must be sufficiently robust to withstand the mechanical stress employed by using a dose-dispensing machine.

The present inventors have found that it is possible to apply a thin film coating on the tablets in order e.g. to increase the swallowability or in order to minimize any dust problems or problems relating to crushing strength or friability. To this end it should be noted that application of a film coating cannot repair substantial problems with respect to crushing strength or friability, but it can just give the final push in the right direction. Furthermore, only a thin film coating must be applied in order to maintain an acceptable mouthfeel, i.e. the coating may be applied in an amount that corresponds to an increase in weight of the tablet of at the most about 2% w/w such as, e.g., at the most about 1.5% w/w, at the most about 1% w/w or in a range of from about 0.25% to 0.75% w/w based on the weight of the uncoated tablets.

In the following are given dimensions of marketed tablets containing calcium carbonate Dimensions of calcium carbonate containing tablet

| | Length [mm] | Height [mm] | Width [mm] |
|---|---|---|---|
| Calcipos-D swallowable (oval/capsule) | 19.3 | 5.6 | 8.7 |
| Calcipos-D chewing tablet (round) | 17.2 | 7.0 | — |
| Calcichew chewing tablet (round) | 16.1 | 7.0 | — |
| Ideos chewing tablet (quadratic) | 19.6 | 4.8 | 19.6 |

The following non-limiting examples are meant to illustrate the present invention.

LEGENDS TO FIGURES

Figure 15:
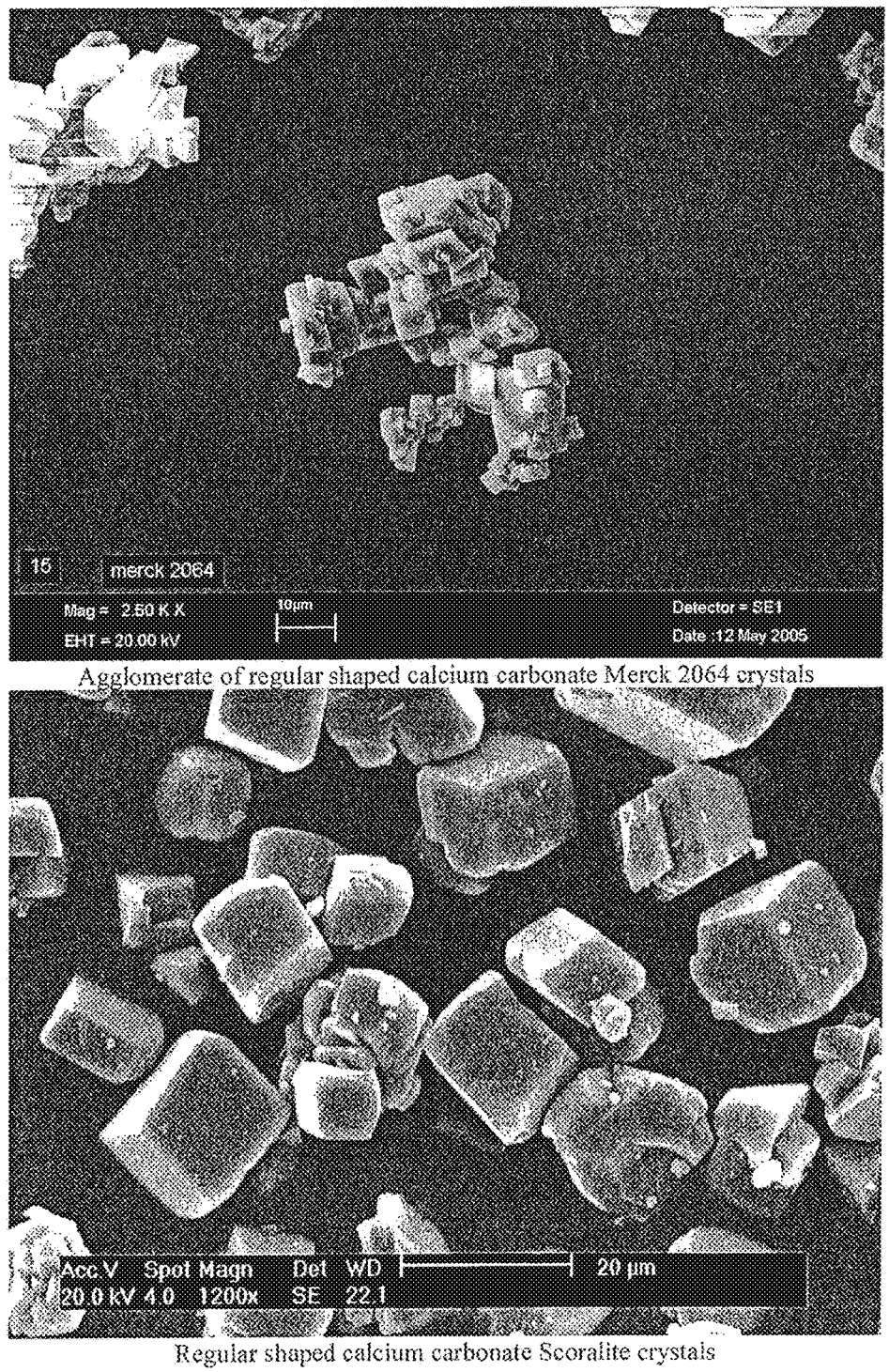

FIG. 15. SEM photos of regularly shaped calcium carbonate crystals (Merck 2064 and Scoralite, respectively)

Figure 16:
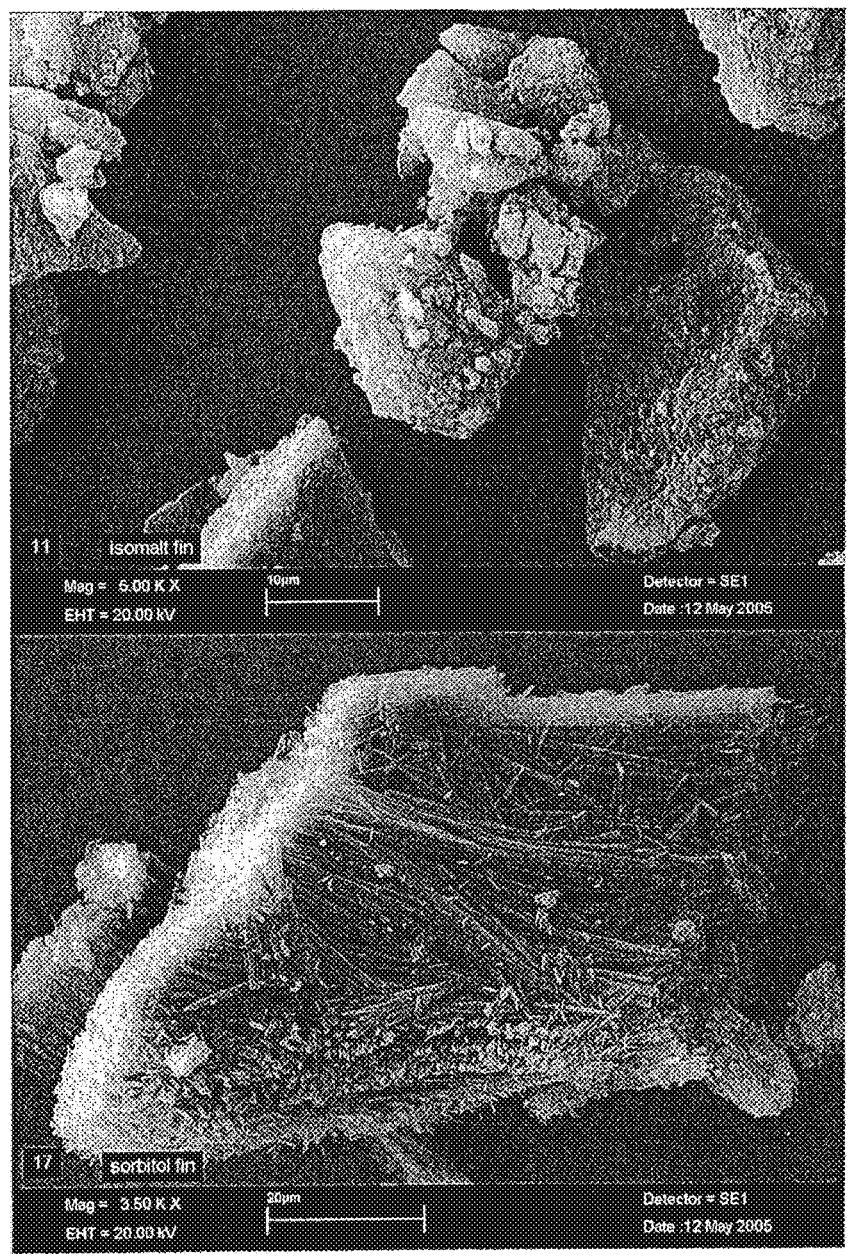

FIG. 16. SEM photos of sugar alcohols having a micro structure (isomalt and sorbitol, respecitvely)

FIG. 17. SEM photos of sugar alcohols that do not have a micro structure (maltitol, xylitol and mannitol, respectively)

FIG. 18. SEM photos of roller compacted material consisting of Scoralite and sorbitol and Merck 2064 and xylitol, respectively.

Figure 19:
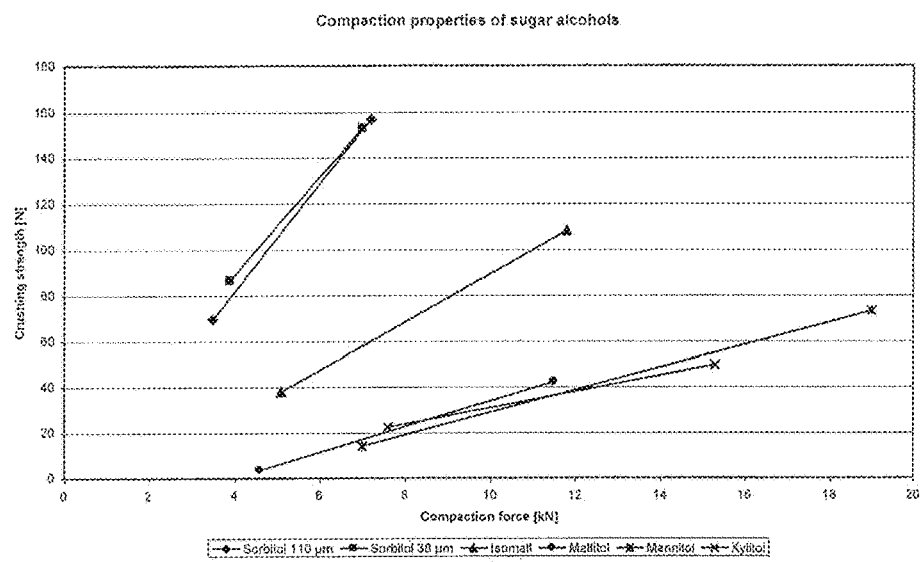

FIG. 19. Compaction properties of sugar alcohols.

Figure 20:
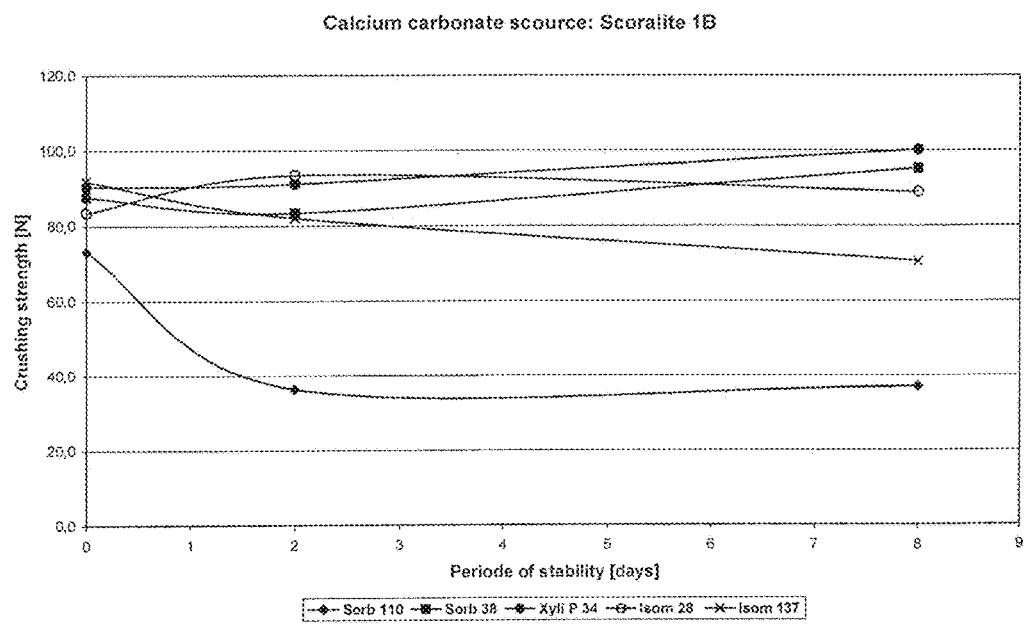

FIG. 20. Stability using Scoralite 1B.

Figure 21:
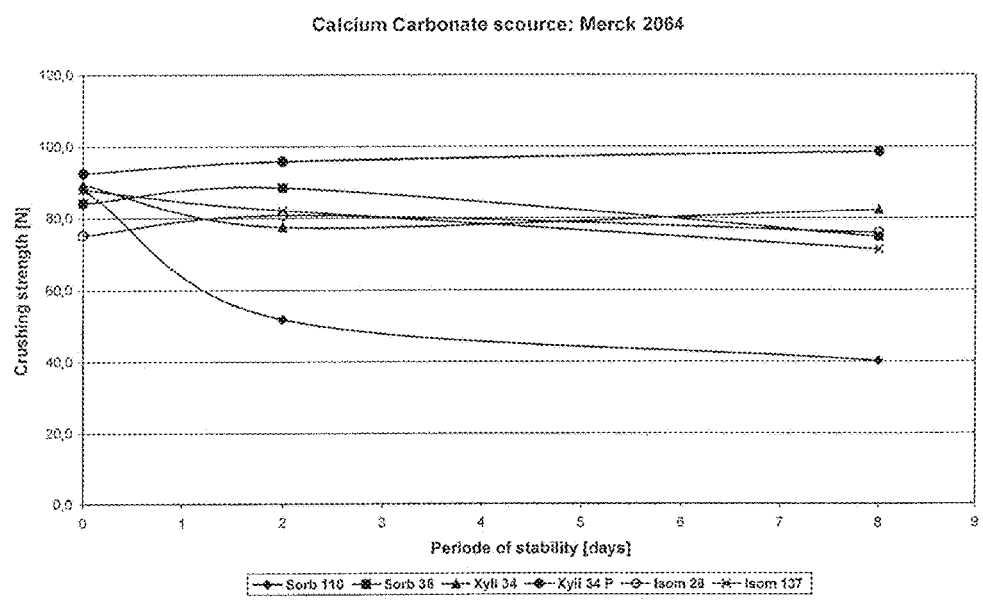

FIG. 21. Stability using Merck 2064.

Figure 22:
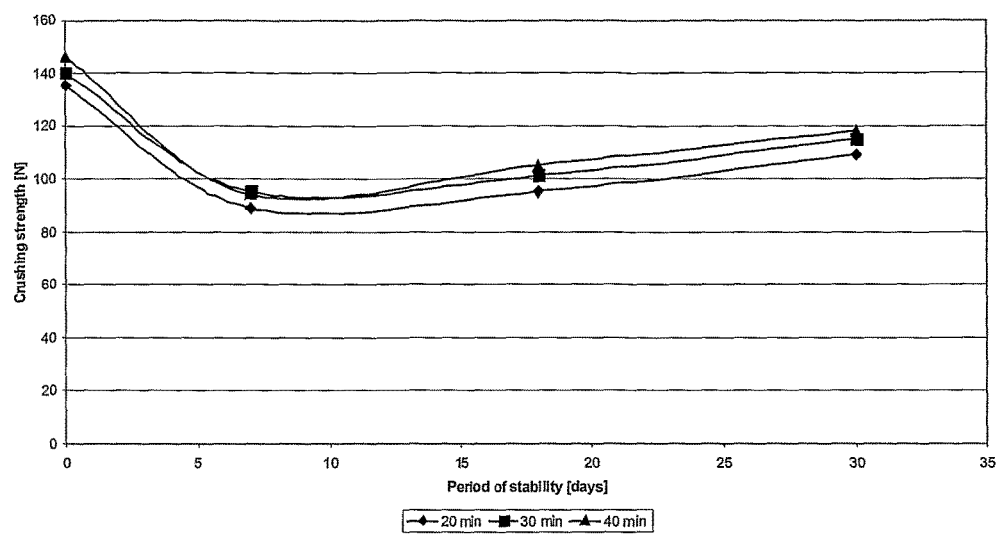

FIG. 22. Impact of mixing time on crushing strength stability

Figure 23:
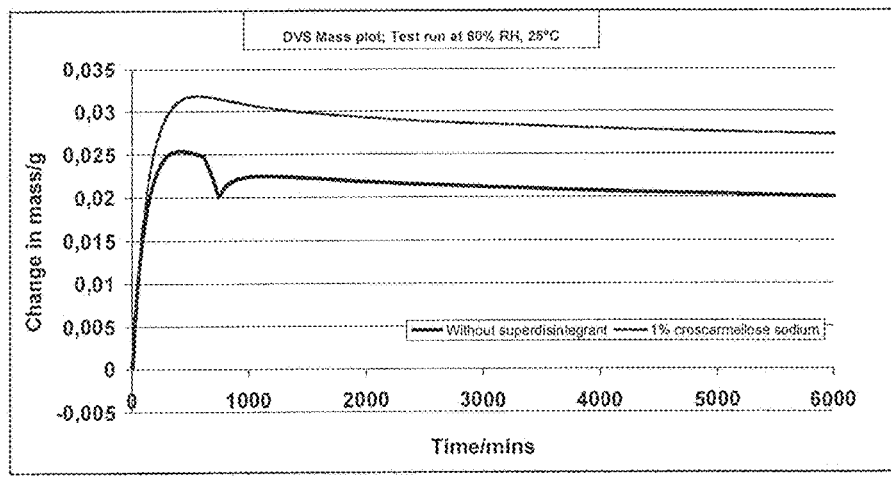

FIG. 23. DVS Mass plot showing the water up-take in the presence and absence of a superdisintegrant.

Figure 24:
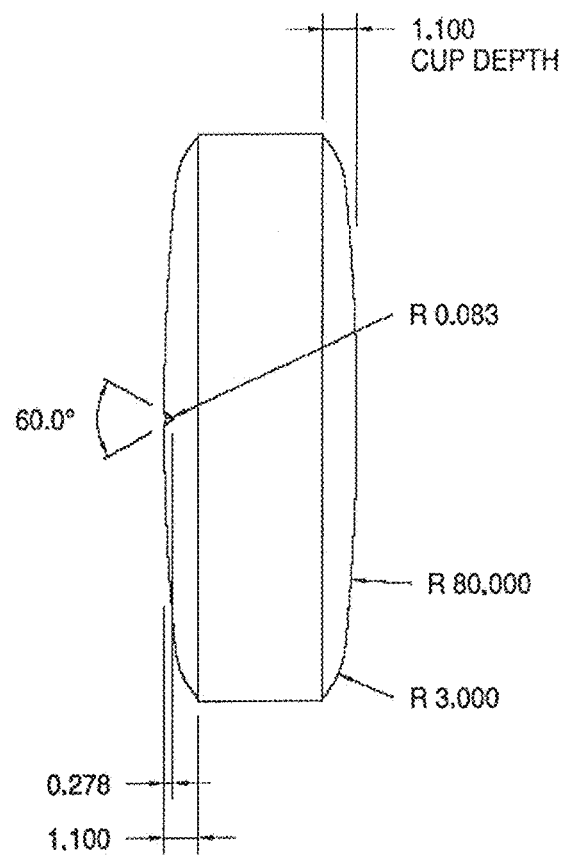

FIG. 24 shows suitable design and dimensions of a tablet according to the invention.

Figure 25:
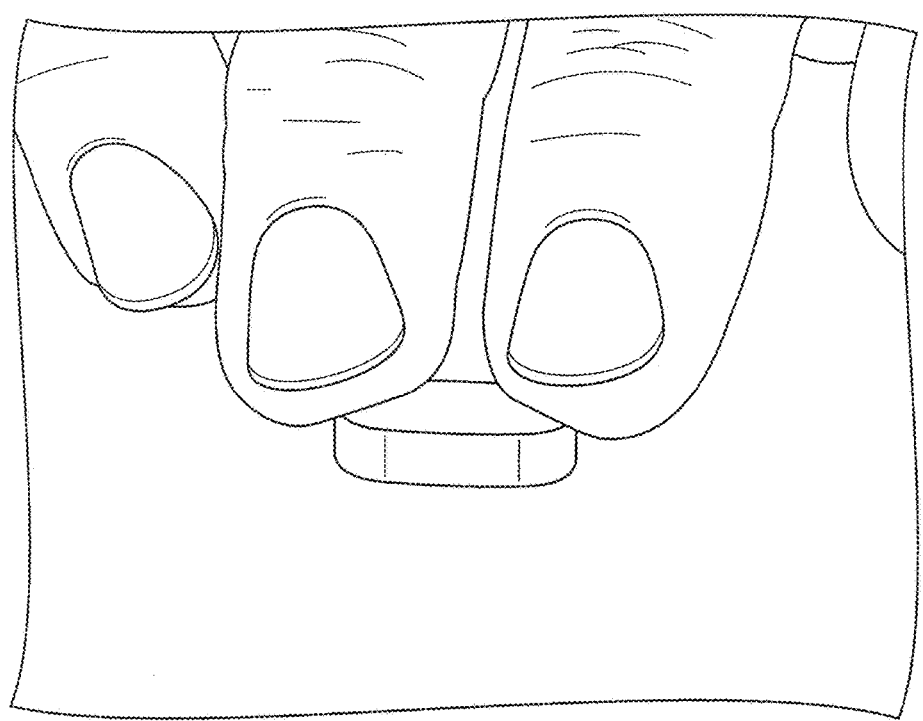

FIG. 25 shows how to break a tablet into two parts of essentially the same size by providing a pressure at both ends. The tablet has a design as shown in FIG. 24.

FIG. 26A shows the length/diameter of a round tablet.

FIG. 26B shows the thickness of the round tablet.

FIG. 26C shows the length/diameter of an oval tablet.

FIG. 26D shows the thickness of an oval tablet.

FIG. 26E shows the width of an oval tablet.

| List of materials | | |
|---|---|---|
| Raw material | Trade name | Vendor |
| Calcium carbonate | Scoralite 1B | Scora Watrigant, SA, France |
| | Merck 2064 | Merck, Darmstadt, Germany |
| Sorbitol | Neosorb P100T Mean particle size: 110 μm (coarse) | Roquette Freres, France |
| | Sorbidex P1666BO Mean particle size: 38 μm (fine) | Cerestar |
| | Sorbidex P16656 Mean particle size: 300 μm | |
| Xylitol | Xylitol CM50 | Danisco Sweeteners |
| Isomalt | Isomalt ST-PF: 28 μm (fine) | Palatinit GmbH, Mannheim, Germany |
| | Isomalt DC100: 137 μm (coarse) | |
| Mannitol | Mannitol 60 | Roquette Freres, France |
| Maltitol | Maltisorb P90 | Roquette Freres, France |
| Povidone K 30 | Povidone K 30 | BASF |
| Povidone K 90 | Povidone K 90 | BASF |
| Cellulose Microcrystalline Type M101 | Cellulose Microcrystalline Type M101 | Mingtai Chemical, Taiwan |
| Pregelatinized Maize Starch | Starch 1500 | Colorcon |
| Crosscarmellose Sodium | Primellose | DMV International |
| Acesulfame Potassium | SweetMaster Ace Fine Grade | Brøste A/S, Denmark |
| Flavour lemon | Flavour Lemon Powder | Firmenich, Schwitzerland |
| Flavour granulate lemon | | Nycomed |
| Flavour granulate orange | | Nycomed |
| Aspartame | Ajinomoto powder | Multi Chem Wallinco (Norway) |
| D3 vitamin | D3-vitamin, Cholecalciferol 100 | Roche |
| Magnesium Stearate | Magnesium stearate | Peter Greven, Netherlands |
| Hypromellose 15 | Methocel E15 | Dow |
| Talc | Talc | Luzenac, Italy |
| Propylene glycol | Propylene glycol | Lyondell Chemie, France |
| Glycerol distearat Type I EP | Precirol ATO 5 | Gattefossé, France |

EXAMPLES

Example 1

Investigation of the Influence on Tablet Strength of Intragranular Admixing of Sorbitol The investigations were based on the following formulation:

TABLE 1

| | Formulation | |
|---|---|---|
| 1 | Calcium Carbonate (Scoralite) | 71.40% |
| 2 | Sorbitol (110 μm) | 22.28% |
| 3 | Povidone K30 | 2.08% |
| 4 | Aspartame | 0.06% |
| 5 | Cholecalciferol - sieved 250 μm (Vitamin $D_3$) | 0.25% |
| 6 | Flavour granulate orange | 3.60% |
| 7 | Magnesium Stearate | 0.34% |

Sorbitol was lump breaked in a Cone Mill (Quadro U20) and afterwards premixed with Calcium Carbonate in a high-shear mixer (Diosna P250 at low impeller speed and no chopper) for 60 sec.

The premix was granulated on a roller compactor (Gerteis 3W-Polygran), and the compacted granules was then mixed with Povidone K30, Aspartame, $D_3$ Vitamin and Flavour in a high-shear mixer (Diosna P250 at low impeller speed and no chopper) for 60 sec. Finally, lubrication with Magnesium Stearate was done a high-shear mixer (Diosna P250 at low impeller speed and no chopper) for 25 sec.

The roller compaction was based on a setup with knurled rollers and control. The key set up parameters are: Gap Width (GW), Force (F), Roller Speed (RS) and screen size.

The particulate material obtained was a granulate that was tabletted on a Fette PT1090 fully instrumented tablet press with a 16 mm round standard concave tablet design. Tablet weight was approximately 1,750 mg. All in-process weight and hardness data are obtained using a Schleuniger AT4.

In this example conditions for the roller compaction was the following:

TABLE 1

| Roller compaction conditions | | | |
|---|---|---|---|
| | H310001 sb. 10 | H314301 sb. 02 | H314301 sb. 08 |
| GW, mm | 3.5 | 2.0 | 3.0 |
| F, kN/cm | 12 | 8 | 20 |
| RS, rpm | 10 | 5 | 5 |
| Screen size, mm | 1.5 | 1.5 | 1.5 |
| Sorbitol admixed | Intra granular | Extra granular | Extra granular |

Figure 1:
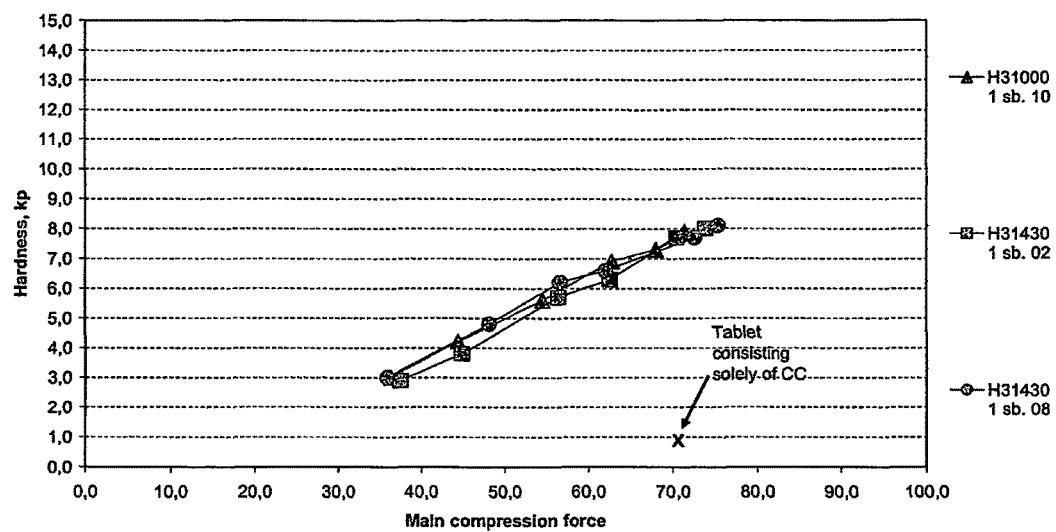
FIG. 1 shows the use of intra granular, extra granular sorbitol or no sorbitol as binder. Investigation of tablet hardness as a function of compression pressure.

The impact on tablet hardness of having admixed sorbitol (having a mean particle size, determined by use of a Malvern laser sizer, of approx 110 μm) compared to not admixing the sorbitol is shown in FIG. 1.

In FIG. 1 it is shown that the presence of sorbitol leads to increased tablet hardness values when compared to tablets consisting solely of calcium carbonate. Furthermore, it is illustrated that admixing the sorbitol 110 μm intra- or extra granular has the same impact on tablet hardness.

Example 2

Impact on Tablet Strength of Variation in Roller Compaction Force

This experiment was carried out according to Example 1 with the variations as described in Table 2.

TABLE 2

| The actual values for GW, F, RS and screen size | | | |
|---|---|---|---|
| | H326501 sb. 3 | H326501 sb. 07 | H326501 sb. 11 |
| GW, mm | 4.0 | 4.0 | 4.0 |
| F, kN/cm | 4 | 8 | 12 |
| RS, rpm | 15 | 15 | 15 |
| Screen size, mm | 1.5 | 1.5 | 1.5 |

Furthermore, the sorbitol had a mean particle size around 38 μm.

Figure 2:
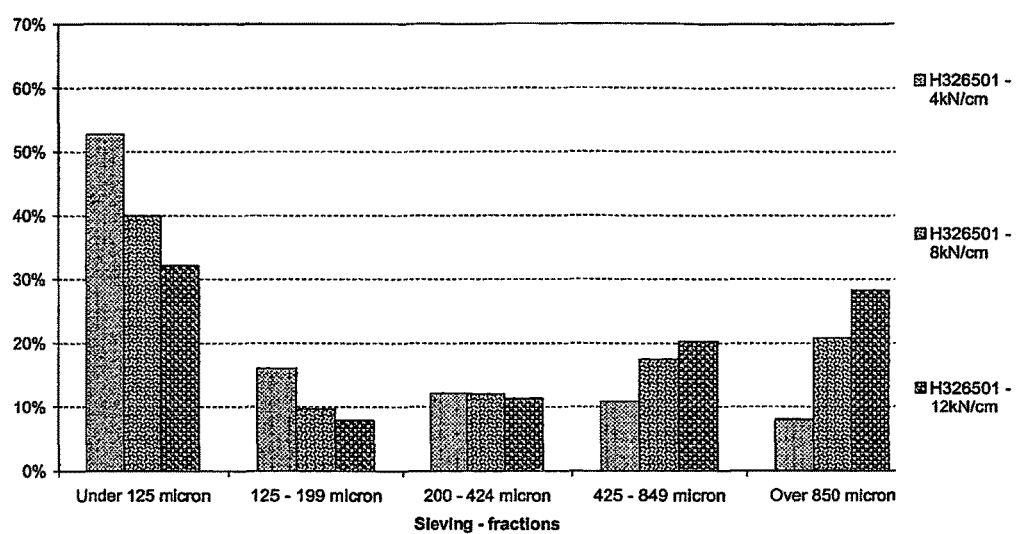
FIG. 2 shows the impact of compaction force on particle size distribution.
Figure 3:
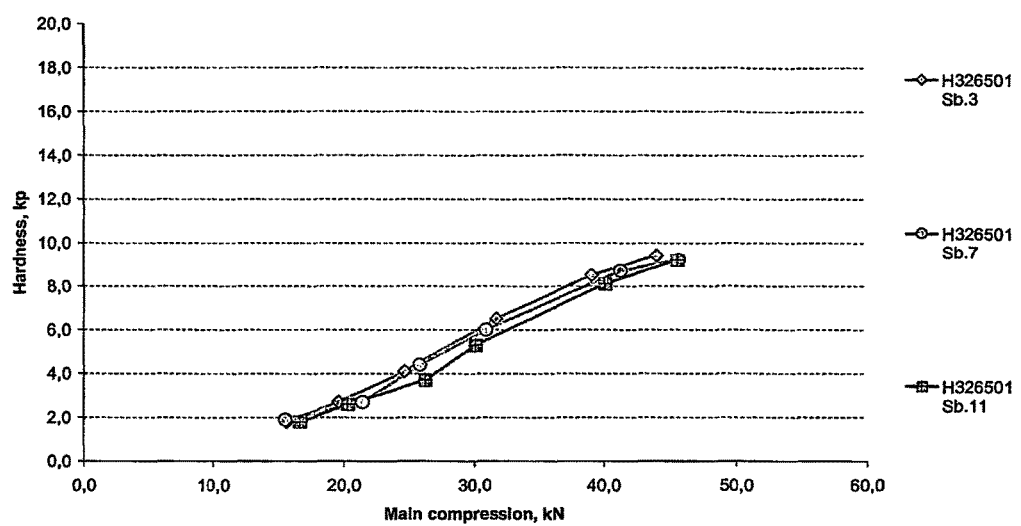
FIG. 3 shows the impact on tablet hardness of variations in particle size distribution of granulate.

The resulting particle size distribution and hardness profiles are shown in FIGS. 2 and 3.

From FIGS. 2 and 3 it is illustrated that even though a variation in roller compaction force leads to a variation in particle size, the tablet hardness profiles remain unaltered. However, an increase in compaction force will improve flowability of the granulate due to a reduction in the fraction below 125 μm.

Example 3

Impact on Tablet Strength of Variation in Particle Size of Sorbitol

This experiment was carried out according to Example 1 with the following variations:

The actual values for GW, F, RS and screen size were the following:
GW 3.5 mm,
F 12 kN/cm,
RS 10 rpm,
Screen size 1.5 mm.

Three qualities of sorbitol was used, having mean particle sizes around 11 μm or 38 μm or 110 μm. The 11 μm and 38 μm qualities were obtained by milling the 110 μm quality.

The tablet design was 14 mm round concave with double radius.

Figure 4:
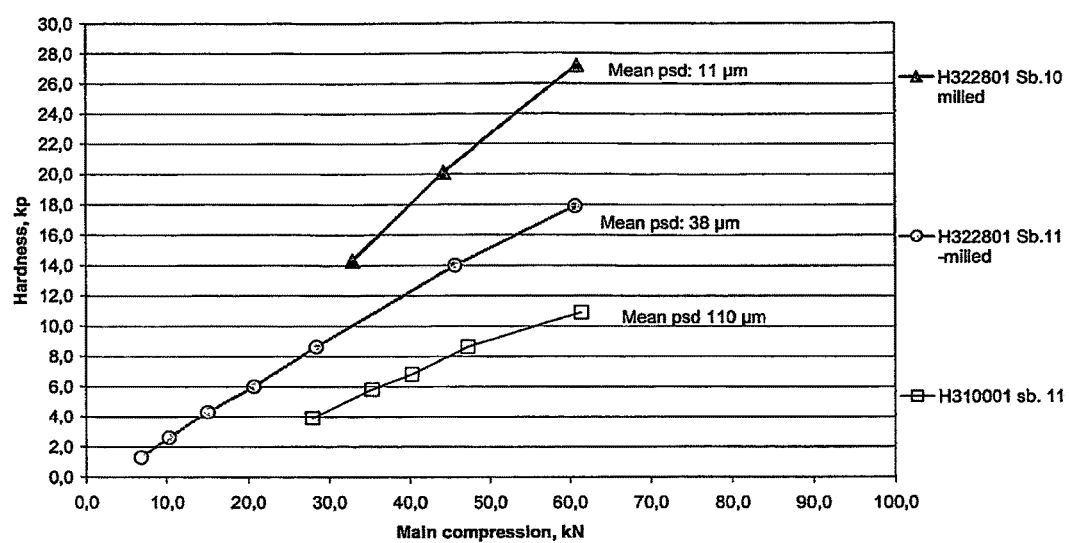
FIG. 4 shows the variation in particle size of sorbitol. Investigation of tablet hardness as a function of compression pressure.

The impact of the variations in particle size of sorbitol is shown in FIG. 4.

From FIG. 4 it is seen that decreasing the size of sorbitol leads to markedly increased tablet hardness for fixed compression force.

Example 4

Impact on Tablet Strength of Variation in Intra-granular Concentration of Sorbitol and Presence of Microcrystalline Cellulose This experiment was carried out according to Example 1 with the following variations as described in Table 3 and Table 4. The roller compaction were in all cases carried out on calcium carbonate and sorbitol alone, where after the other excipients listed were admixed.

TABLE 3

| The formulation used | | | |
|---|---|---|---|
| | H335528 | H404302 | H407504 |
| Calcium carbonate, Scoralite | 67.5% | 71.4% | 80.1% |
| Sorbitol, 38 μm | 21.1% | 22.3% | 15.5% |
| Mixing ratio - Calcium:Sorbitol | 3.2:1 | 3.2:1 | 5.2:1 |
| Cellulose Microcrystalline Type M101 | 6.6% | | |
| Starch 1500 | 4.2% | | 3.4% |
| Acesulfam Potassium | 0.1% | | 0.1% |
| Flavour Lemon | 0.3% | | 0.5% |
| Povidone K30 | | 2.1% | |
| Aspartame | | 0.1% | |
| Vitamin D3 | | 0.3% | |
| Flavour granulate orange | | 3.6% | |
| Magnesium stearate | 0.3% | 0.3% | 0.4% |

TABLE 4

| The actual values for GW, F, RS and screen size | | | |
|---|---|---|---|
| | H335528 | H404302 | H407504 |
| GW, mm | 3.5 | 4.0 | 3.5 |
| F, kN/cm | 12 | 12 | 12 |
| RS, rpm | 15 | 15 | 3 |
| Screensize, mm | 1.5 | 1.5 | 1.5 |

Figure 5:
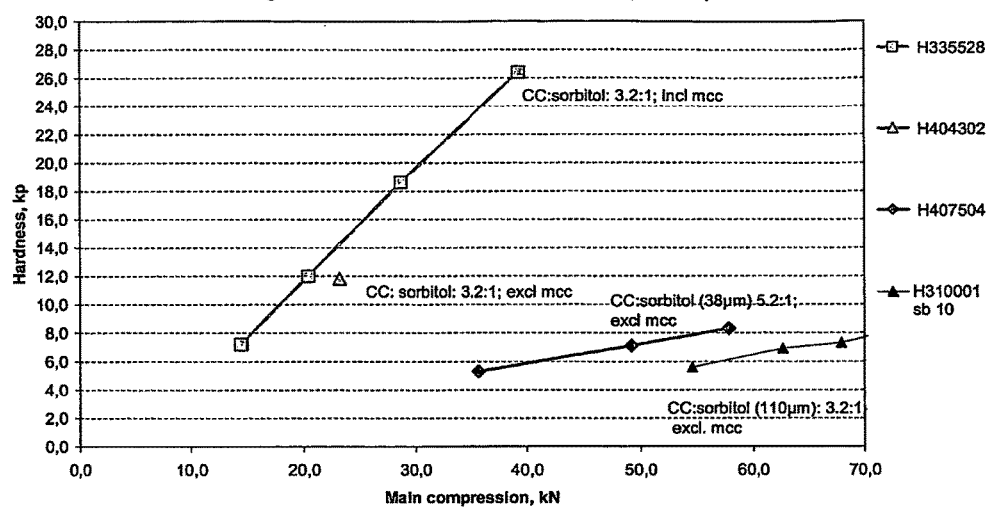
FIG. 5 shows the variation in amount of sorbitol and addition of microcrystalline cellulose. Investigation of tablet hardness as a function of compression pressure.

FIG. 5, which includes batch H310001 sb10 from Example 1 shows the impact on tablet hardness when the amount and particle size of sorbitol used are varied. This illustrates that it is important to have sorbitol distributed as completely as possible between the calcium particles. Inappropriate distribution will be the result of too large a particle size or too low a concentration. Furthermore, FIG. 5 illustrates that the impact of cellulose microcrystalline (mcc) on tablet hardness is minor compared to the influence of sorbitol.

Example 5

Impact on Tablet Strength of Moisture Content in the Surrounding Air when Using Sorbitol as Binder This experiment was carried out according to Example 1 with the following variations as described in Table 5.

TABLE 5

The actual values for GW, F, RS and screen size

|  | H310001 sb. 11 | H315501 sb. 02 | H322801 sb. 02 dried |
|---|---|---|---|
| GW, mm | 3.5 | 3.5 | 3.5 |
| F, kN/cm | 12 | 16 | 12 |
| RS, rpm | 10 | 10 | 10 |
| Screen size, mm | 1.5 | 1.5 | 1.5 |

Further, the tablet design was 14 mm round concave with double radius.

The manufacturing was carried out during winter and summer conditions. During winter condition RH in the surrounding air was below 50%, whereas in the summer period the RH was above 70%.

Figure 6:
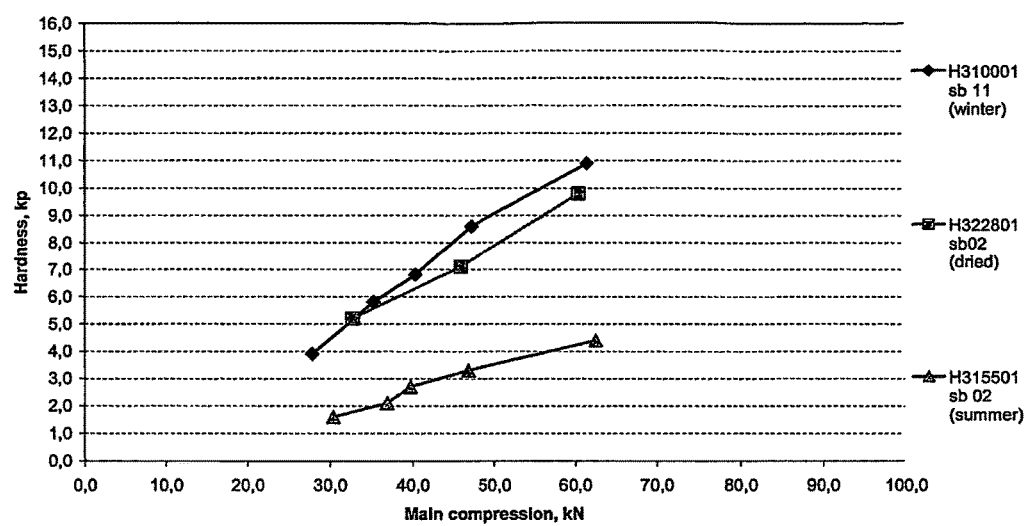
FIG. 6 shows the impact of moisture content of surrounding air on tablet hardness.

The impact on tablet hardness of variation in moisture content in the surrounding air is shown in FIG. 6.

FIG. 6 shows that the granulate is very sensitive to moisture, when sorbitol having a mean particle size of 110 μm is used.

Tablets based on sorbitol having a mean particle size of approx. 38 μm did not show sensitivity towards the time of the year at which the tabletting was carried out.

Example 6

Bulk Density of Roller Compacted Formulations Containing a Calcium Salt

Changes in bulk density as a consequence of roller compaction are shown in Table 6.

TABLE 6

Changes in bulk density

| Density mixture (g/cm³) | Density roller compacted granulate (g/cm³) |
|---|---|
| 0.99 | 1.08 |

Based on data in the table above it is clear that the increase in density caused by the roller compaction process is minimal.

This experiment was carried out according to Example 1 with the following variations:
Only the granulate was produced. The admixing of povidone 30, aspartame, D3 vitamin and flavour was omitted.

The actual values for GW, F, RS and screen size were the following

| GW, mm | 3.5 |
|---|---|
| F, kN/cm | 12 |
| RS, rpm | 10 |
| Screen size, mm | 1.5 |

Example 7

Influence of Variations in the Type of Binder Used on Tablet Hardness

This experiment was carried out according to Example 1 with the following variations as described in Table 7 and Table 8. The roller compaction was in all cases carried out on calcium carbonate and either sorbitol or maltitol, whereafter the other excipients listed were admixed.

TABLE 7

The formulation used

|  | H335525 | H335528 |
|---|---|---|
| Calcium carbonate, (Scorallite) | 75.3% | 67.5% |
| Sorbitol, 38 μm |  | 21.1% |
| Maltitol | 13.3% |  |
| Cellulose microcrystalline, type M101 | 6.6% | 6.6% |
| Starch 1500 | 4.2% | 4.2% |
| Acesulfame Potassium | 0.1% | 0.1% |
| Lemon flavour | 0.3% | 0.3% |
| Magnesium stearate | 0.3% | 0.3% |

TABLE 8

The actual values for GW, F, RS and screen size

|  | H335525 | H335528 |
|---|---|---|
| GW, mm | 3.5 | 3.5 |
| F, kN/cm | 12 | 12 |
| RS, rpm | 3 | 15 |
| Screen size, mm | 1.5 | 1.5 |

Further, the tablet design was capsule shaped 9.4 mm*18.9 mm.

Figure 7:
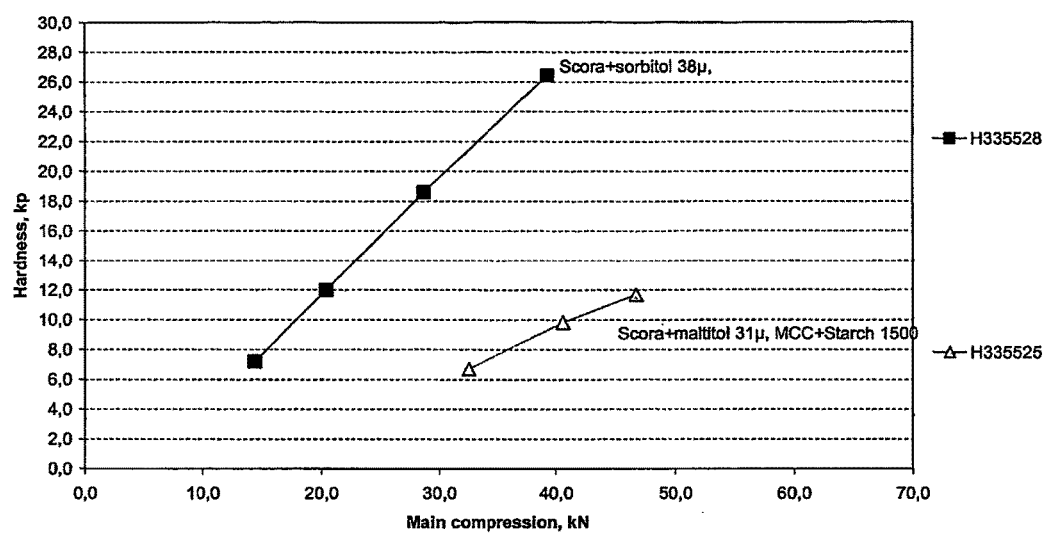
FIG. 7 shows the impact on tablet hardness of addition of other sugar alcohols, that is maltitol.

The resulting hardness profiles are shown in FIG. 7.

From FIG. 7 it is seen that the use of maltitol as binder does not impart as good binding properties as that obtained when sorbitol is employed.

Example 8

Impact on Tablet Hardness of Non-optimal Admixing of Sorbitol

This experiment was carried out according to Example 1 with the variations as described in Table 9.

TABLE 9

The actual values for GW, F, RS and screen size were the following:

|  | H326501 sb. 11 | G334701-a | G/H404301 | G/H404302 |
|---|---|---|---|---|
| GW, mm | 4.0 | 3.5 | 4.0 | 4.0 |
| F, kN/cm | 12 | 12 | 12 | 12 |

TABLE 9-continued

The actual values for GW, F, RS and screen size were the following:

|  | H326501 sb. 11 | G334701-a | G/H404301 | G/H404302 |
|---|---|---|---|---|
| RS, rpm | 15 | 15 | 15 | 15 |
| Screen size, mm | 1.5 | 1.5 | 1.5 | 1.5 |
| Sorbitol lump breaked | Yes | No | Yes | Yes |

Sorbitol had a mean particle size about 38 μm.

Figure 8:
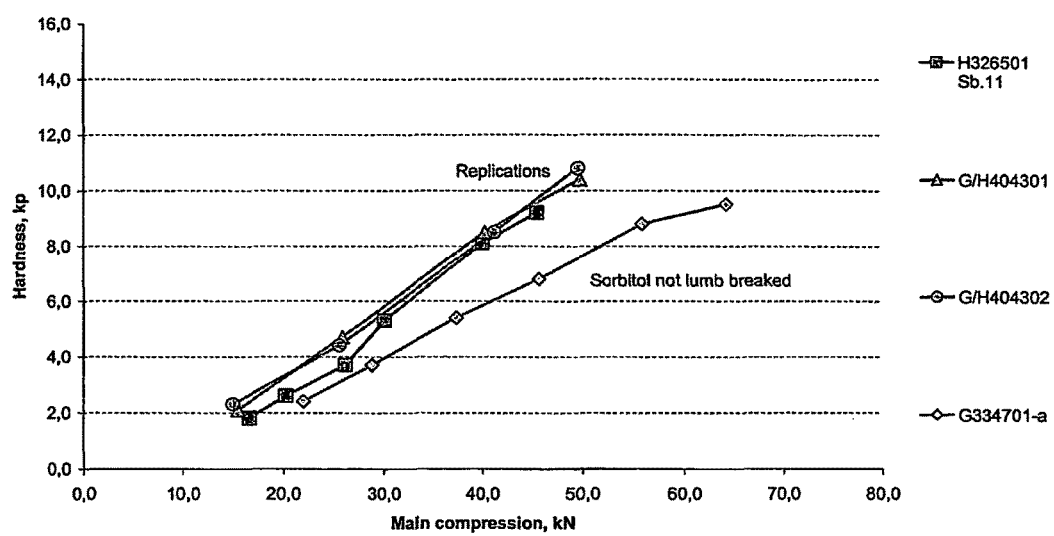
FIG. 8 shows the impact on tablet hardness of omitting lumb breaking of 38 μm sorbitol.

FIG. 8 shows the impact on tablet hardness of adding sorbitol that has not been lumb breaked before the admixture.

From FIG. 8 it is seen that lump breaking is important. Furthermore, this illustrates the importance of getting an optimal distribution of sorbitol particles between the calcium particles.

Having an optimal distribution, the tablet hardness is very reproducible as also shown in FIG. 8.

Example 9

Investigation of $D_3$ Vitamin Assay of Tablets Based on Intra-granular Admixing of Fine Particle Sized Sorbitol This experiment was carried out according to Example 1 with the variations as described in Table 10.

TABLE 10

The actual values for GW, F, RS and screen size

|  | H328001 sb. 01 | H328001 sb. 02 |
|---|---|---|
| GW, mm | 4.0 | 4.0 |
| F, kN/cm | 8 | 12 |
| RS, rpm | 15 | 15 |
| Screen size, mm | 1.25 | 1.5 |

Sorbitol had a mean particle size around 38 μm.

Figure 9:
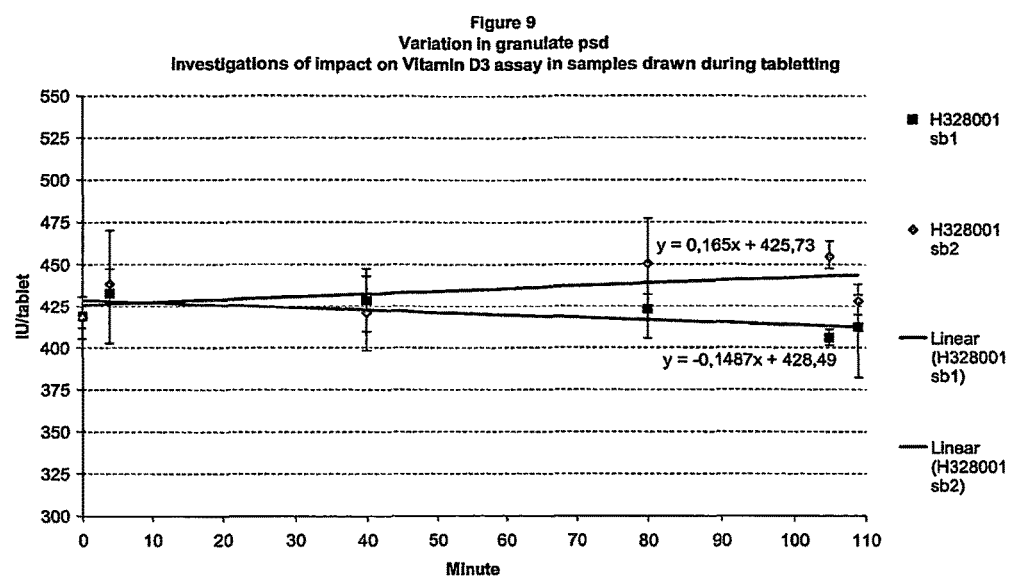
FIG. 9 shows the variation in granulate pad. Investigation of impact on vitamin $D_3$ Vitamin assay in samples drawn during tabletting.

In FIG. 9 the D3 vitamin assay results from sampling over 2 hours of compression has been illustrated. It can be seen that the admixing of a small amount of D3 vitamin is possible in production scale. The slopes of the trend lines are close to 0 and almost identical for the 2 batches tested in this example.

Example 10

Impact on Tablet Hardness of the Admixing of the Binder Povidone K 30, a Typical Example of a Wet Binder This experiment was carried out according to Example 1 with the variations as described in Table 11 and Table 12.

TABLE 11

The actual values for GW, F, RS and screen size

|  | H310002 sb. 17 | H310002 sb. 19 | H310003 sb 17 | H310003 sb 19 |
|---|---|---|---|---|
| GW, mm | 3.5 | 3.5 | 3.5 | 3.5 |
| F, kN/cm | 8 | 8 | 8 | 8 |
| RS, rpm | 10 | 10 | 10 | 10 |
| Screen size, mm | 1.5 | 1.5 | 1.5 | 1.5 |

TABLE 12

Changes of the composition and tabletting

|  | H310002 sb. 17 | H310002 sb. 19 | H310003 sb 17 | H310003 sb 19 |
|---|---|---|---|---|
| +/−Povidone K 30 | + | + | − | − |
| Tablet design | 16 mm round, concave | 14 mm round, concave double radius | 16 mm round, concave | 14 mm round, concave double radius |

Figure 10:
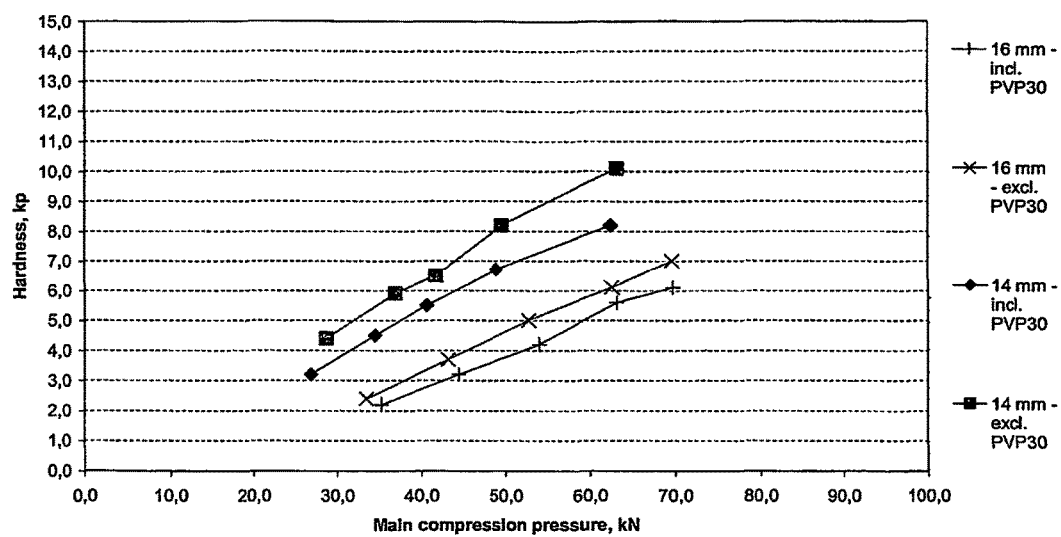
FIG. 10 shows the impact on tablet hardness of admixing of Povidone K 30.

FIG. 10 shows that the admixing of dry Povidone K 30 has no beneficial impact on the tablet hardness.

Example 11

Impact on Tablet Hardness of Variation in Type of Calcium Carbonate and Type and Particle Size of Sugar Alcohol This experiment has been carried out as described below:

In all the below described experiments 1-24 the amount of calcium salt is 76.22% w/w of the final tablet mass, the amount of sugar alcohol is 23.78% w/w, with the exception of experiments 4 and 20 at which the 23.78% w/w of sugar alcohol is replaced with 14.63% w/w of sugar alcohol and 9.15% w/w of Precirol. The actual type of calcium source and the type of sugar alcohol is described in Table 13.

TABLE 13 types of calcium and sugar alcohol source

| Experiment no.: | Calcium salt Source | Sugar alcohol, source and ps* | Sugar alcohol Figure legend |
|---|---|---|---|
| 1 | Scoralite | Sorbitol, 38 μm | Sorb38 |
| 2 | Scoralite | Sorbitol, 110 μm | Sorb110 |
| 3 | Scoralite | Xylitol, 34 μm | Xyli34 |
| 4 | Scoralite | Xylitol, 34 μm and Precirol | Xyli34P |
| 5 | Scoralite | Isomalt, 28 μm | Isom28 |
| 6 | Scoralite | Isomalt, 137 μm | Isom137 |
| 7 | Scoralite | Mannitol, 48 μm | Mann48 |
| 8 | Scoralite | Maltitol, 31 μm | Malt31 |
| 17 | Merck 2064 | Sorbitol, 38 μm | Sorb38 |
| 18 | Merck 2064 | Sorbitol, 110 μm | Sorb110 |
| 19 | Merck 2064 | Xylitol, 34 μm | Xyli34 |
| 20 | Merck 2064 | Xylitol, 34 μm and Precirol | Xyli34P |
| 21 | Merck 2064 | Isomalt, 28 μm | Isom28 |
| 22 | Merck 2064 | Isomalt, 137 μm | Isom137 |
| 23 | Merck 2064 | Mannitol, 48 μm | Mann48 |

TABLE 13-continued types of calcium and sugar alcohol source

| Experiment no.: | Calcium salt Source | Sugar alcohol, source and ps* | Sugar alcohol Figure legend |
|---|---|---|---|
| 24 | Merck 2064 | Maltitol, 31 μm | Malt31 |
| 25 | Scoralite | Sorbitol, approx. 300 μm | Sorb300 |
| 26 | Scoralite | Sorbitol, 38 μm | Sorb38 |

*ps: mean particle size (d(v; 0.5) determined by use of a Malvern Mastersizer)

The calcium salt and the sugar alcohol are mixed in a total amount of 6 kg in a Fielder high shear mixer. The sugar alcohol is sieved through sieve size 300 μm prior to mixing. The mixing of 6 kg is done twice and the total yield of 12 kg is mixed in a planetary mixer. Thereafter, the mixtures are roller compacted (intra granular sugar alcohol) using the following values for GW, F, RS and screen size. (For the experiments 25-26 the sugar alcohol is admixed by hand after roller compaction has been carried out (extra granular sugar alcohol)).

| | |
|---|---|
| GW: | 3.5 mm |
| F: | 12 kN/cm |
| RS: | 5 rpm |
| Screen size | 1.5 mm |

The compactate is admixed with 0.34% w/w of magnesium stearate.

Compression is carried out on a Fette 1090 using a 18.9 mm×9.4 mm capsule shaped punch design and a theoretical tablet mass of 1683 mg. For each experiment a correlation between tablet compression force and crushing strength is found. The crushing strength has been measured by use of a Schleuniger Autotest 4 and n=20. The resulting hardness profiles are shown in FIGS. 11-13.

Figure 11:
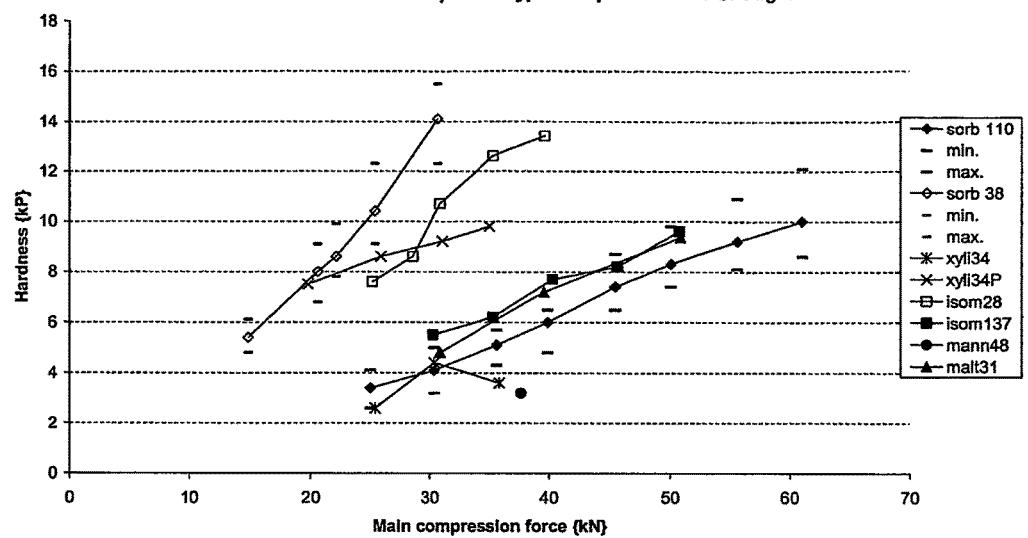
FIG. 11 shows the impact of type and particle size of sugar alcohol. Scoralite is used as calcium source.
Figure 12:
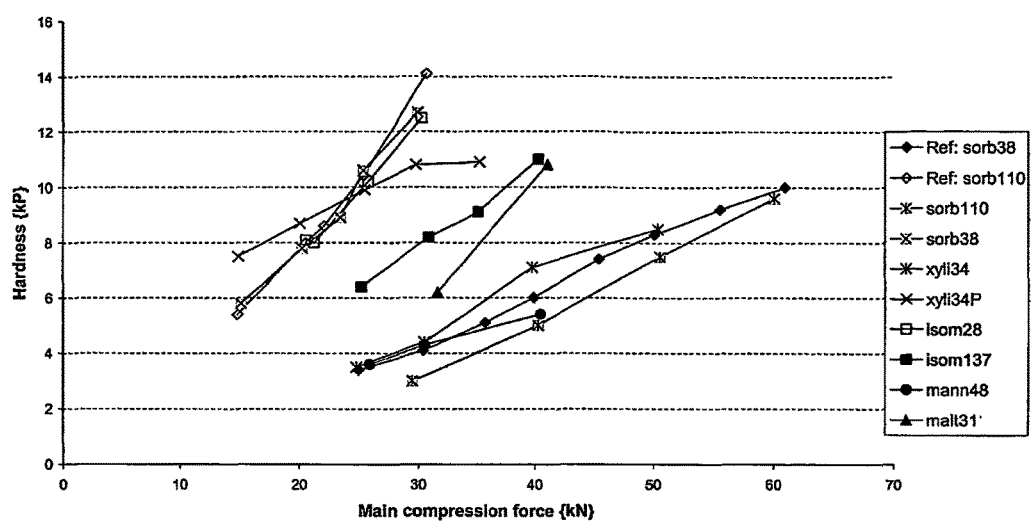
FIG. 12 shows the impact of type and particle size of sugar alcohol. Merck 2064 is used as calcium source.
Figure 13:
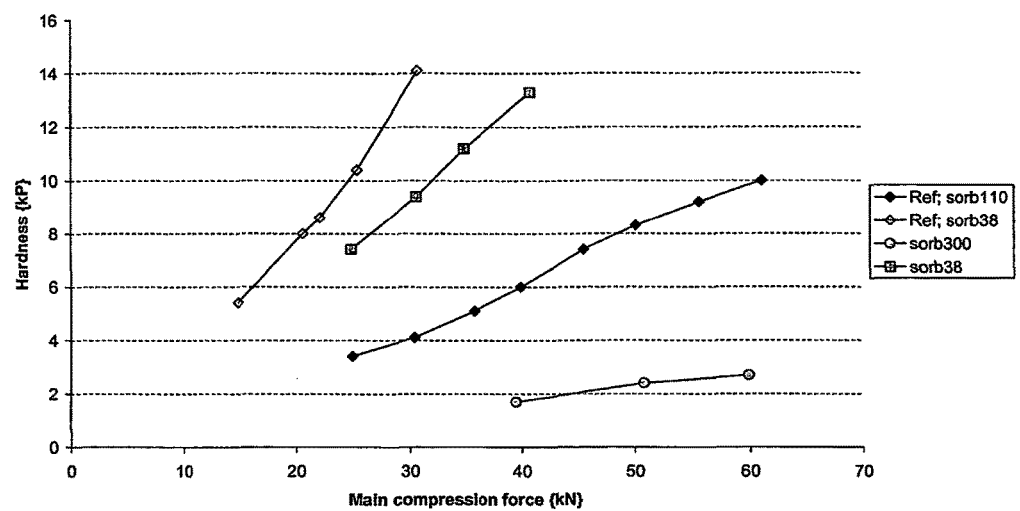
FIG. 13 shows the impact of extra granular admixture of sortitol in different particle sizes. Scoralite is used as calcium source.

From FIGS. 11-12 it is seen that for both the Scoralite and Merck 2064 calcium carbonates intra granular admixed fine particular sorbitol or isomalt results in tablets with a much higher crushing strength than can be obtained with xylitol, mannitol, maltitol or coarse particular sorbitol and isomalt. Furthermore it was observed during the experiment that the use of mannitol, xylitol or maltitol leads to tablets with a tendency of capping.

Without being bound by theory the impact of different sugar alcohols on tablet crushing strength can be described as being dependent on their binding properties and distribution throughout the tablet. The distribution of the sugar alcohol throughout the tablet is crucial, as regular shaped calcium carbonate crystals, see FIG. 15, are not likely to establish the adherence necessary for obtaining a coherent tablet. Sugar alcohols capable of obtaining a homogeneous distribution throughout the tablet are especially suitable. Examples of such sugar alcohols are sorbitol and isomalt as illustrated in FIG. 16 where it is shown that the individual crystals of sorbitol and isomalt have a micro structure or a non-compact micro structure, i.e. the individual crystals have some deformation capacity to be squeezed between other kinds of particles. This is in contrast to the crystals of mannitol, maltitol and xylitol where the same kind of micro structure cannot be found, as illustrated in FIG. 17. This micro structure is assumed facilitate a further distribution throughout the tablet by breakage during the tablet compression. The distribution of sugar alcohol made possible by this micro structure is shown in FIG. 18. Therefore, calcium carbonate containing tablet comprising sugar alcohols with the described micro structure are much more likely to be coherent tablets, with a satisfactory crushing strength, than tablet based on sugar alcohols without the described micro structure.

However, even if a micro structure is present it is required that the particles of the sugar alcohols are sufficiently small which is illustrated in FIGS. 11 and 12 where it can be seen that fine particular sorbitol and isomalt results in tablets with a much higher crushing strength than can be obtained with coarser particles.

Based on the above discussions of the importance of particle size and micro structure of sugar alcohols the results shown in FIG. 13 can easily be explained. Even though tablets illustrated by the curve Sorb300 are based on the teaching of Pharmaceutical Technology Vol 1 (Tabletting technology, editor M. H. Rubinstein), where instant sorbitol having a particle size distribution of 60-90% between 212-500 μm is admixed as extra granular sugar alcohol, the crushing strength is extremely low even at high compression forces. Crushing strength can be markedly increased by the use of sorbitol with a finer particle size, see FIG. 13 (curve Sorb38). Even though the different punch design of Example 1 makes a direct comparison difficult it is illustrated than when using sorbitol of a 110 μm quality there is no difference between intra and extra granular admixture of sorbitol. Therefore, when using sorbitol as extra granular sugar alcohol the particle size is very critical. This also applies for other sugar alcohols.

Figure 14:
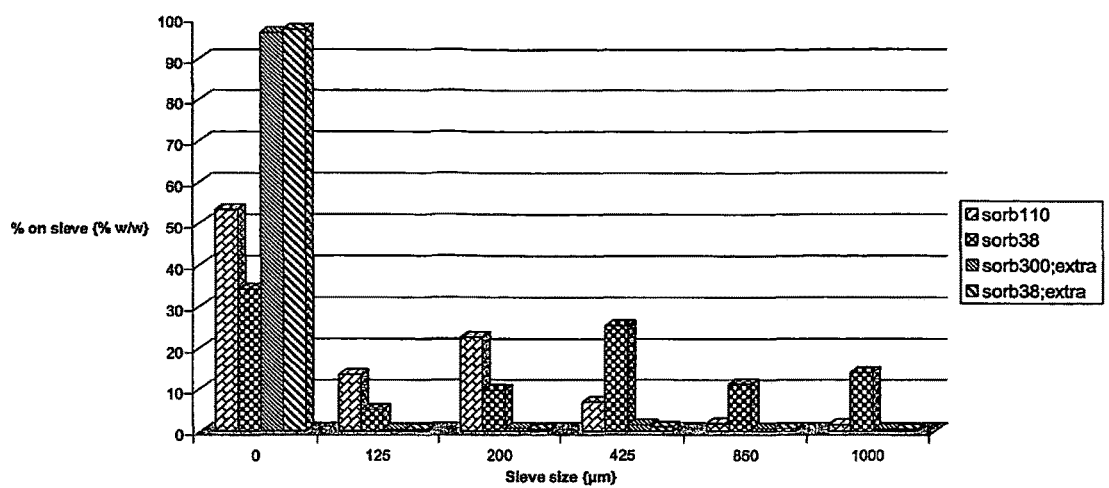
FIG. 14 shows the impact of granular particle size of intra or extra granular admixture of sorbitol. Scoralite is used as calcium source.

However, the compaction of pure calcium carbonate results in a granulate with a very low binding capacity, as illustrated by the very large fraction below 125 μm seen in FIG. 14. This means that by adding sugar alcohol extra granularly instead of intra granularly the final mixture for tabletting will have extremely poor flow properties which will make tabletting in production scale very difficult.

Furthermore it can be seen from FIG. 11 that the addition of Precirol increases the crushing strength without changing the sensitivity of the crushing strength to changes in main compression force, that is Precirol is less optimal as a binder.

Example 12

Test of Compactability of Different Sugar Alcohols

Tablets comprising sorbitol 110 μm, sorbitol 38 μm, isomalt 27 μm, maltitol, mannitol or xylitol were compressed on an instrumented Fette Exacta 1/F single punch tablet press, only maximum compression force on the upper punch was recorded. Before the compression of each tablet the punch tips and the die bore were lubricated with a 5% suspension of magnesium stearate in acetone. The acetone was allowed to evaporate before compression of the tablet.

The sugar alcohol was weighed, transferred to the die bore and then compressed, see Table 14. Immediately after ejection the tablet was tested for crushing strength.

TABLE 14

| Sugar alcohol | Trade name | Tablet weight |
|---|---|---|
| Sorbitol | Neosorb P100T | 530 mg |
| | Sorbidex P1666BO | 400 mg |
| Isomalt | Isomalt ST-PF | 400 mg |
| Maltitol | Maltisorb P90 | 400 mg |
| Mannitol | Mannitol 60 | 400 mg |
| Xylitol | Xylitol CM50 | 400 mg |

It was assumed that the obtained tablet crushing strengths of the sugar alcohols are substantially independent of particle size and this was tested using sorbitol having two different mean particle sizes, 38 µm and 110 µm. From FIG. 19 (each point is the average of three measurements) it is seen that the assumption was correct. Therefore, test of particle size was not repeated for the other sugar alcohols.

From FIG. 19 it can be seen that sorbitol has the best compactability resulting in the steepest slope of the correlation between compression force and crushing strength. Sorbitol is followed by isomalt whereas maltitol, mannitol and xylitol have a very poor compactability. These results support the results discussed in Example 11 and FIGS. 17-18. Therefore, it can be concluded that sugar alcohols having a polycrystal structure results in stronger tablets when compressed than sugar alcohols without a polycrystal structure.

Example 13

Impact on Tablet Crushing Strength Stability of Variation of Calcium Carbonate and Type and Particle Size of Sugar Alcohol Tablets according to Example 11 were manufactured. Tablets with an initial crushing strength between 70 N to 100 N were stability tested. The conditions for the stability testing were storage in open petri dishes at 25° C./60% (25/60) relative humidity (RH) for 14 days. The crushing strength was tested just before the stability test was started and after 2 days, 7 days and 14 days. The crushing strength was measured by use of a Schleuniger-2E Hardness tester, n=10.

Crushing strength stability is shown in FIGS. 20-21.

From FIGS. 20 and 21 it is seen that for both the Scoralite and Merck 2064 calcium carbonates intra granularly admixed fine particular sorbitol or isomalt (both fine and coarse) results in tablets with a satisfactory stability of crushing strength. However the use of coarse sorbitol results in tablets with a decrease in crushing strength during storage in open petri dishes at 25° C./60% RH.

Possible explanations for the observed differences in stability of tablets containing coarse sorbitol or either fine sorbitol or isomalt (both fine and coarse) could be the following: In order to obtain sorbitol containing tablets with the desired initial crushing strength a considerably higher main compression force was needed for tablets containing coarse sorbitol compared to fine. Even though the tablets based on coarse sorbitol were less porous, the crushing strength declined considerably during the first two days of stability testing. This could be caused by a much less homogeneous distribution of the coarse sorbitol in the tablet.

For isomalt the use of either fine or coarse particles in both cases leads to tablets with satisfactory crushing strength stability. This could be caused by the fact that isomalt is considerably less hygroscopic compared to sorbitol.

Example 14

Manufacture of Calcium Carbonate Containing Tablets

Tablets were manufactured according to Example 1 with the below described exceptions. The roller compaction was in all cases carried out on calcium carbonate and sorbitol, where after the other excipients listed were admixed. The film liquid was applied at described below.

Tablet formulation:

TABLE 15

|  | Amount per tablet | | | |
|---|---|---|---|---|
|  | 2 [mg] | [%] | 3 [mg] | [%] |
| Raw material |  |  |  |  |
| Calcium carbonate Scoralite | 1250 | 72.2 | 1250.0 | 71.9 |
| Sorbitol P 1666B0 | 385.5 | 22.3 | 385.5 | 22.2 |
| Cellulose microcryst Type 101 | 75 | 4.3 | 75 | 4.3 |
| Acesulfam Potassium | 1 | 0.1 | 1 | 0.1 |
| Flav. Lemon Powder |  |  | 7.5 | 0.4 |
| Magnesium stearate | 6 | 0.3 | 6 | 0.3 |
| Tablet weight [mg] | 1717.5 |  | 1725.0 |  |
| Film liquid* |  |  |  |  |
| Hypromellose 15 | 7.16 | 0.4 | 7.19 | 0.4 |
| Talc | 4.30 | 0.2 | 4.31 | 0.2 |
| Propylene glycol | 1.43 | 0.1 | 1.44 | 0.1 |
| Water, purified | 130.28 |  | 130.81 |  |

The granulate was compressed on a Fette PT1090 using capsule shaped punches (9.4 mm×18.9 mm).

The film liquid were applied on the tablets in an Accella Coater 150 (Manesty Inc.), by use of the following parameters:

| Inlet air temperature | 50° C. |
|---|---|
| Outlet air temperature | 45° C. |
| Pan rpm | 2.2 |
| batch size | 75 kg |

The obtained tablets had a crushing strength of 133 N and a disintegration time below 12 minutes.

Example 15

Manufacture of Calcium Carbonate Containing Tablets

A granulate was manufactured according to Example 14 with the following exceptions:

TABLE 16

|  | Amount per tablet [mg] | Amount per tablet [%] |
|---|---|---|
| Raw material |  |  |
| Calcium carbonate, Scoralite | 1250.0 | 72.26 |
| Sorbitol 38 µm | 385.0 | 22.26 |
| Cellulose microcryst. Type 101 | 56.0 | 3.24 |
| Croscarmellose sodium | 20.0 | 1.16 |
| Magnesium stearate | 6.0 | 0.35 |
| Acesulfame Potassium | 1.0 | 0.06 |
| Flavour lemon powder | 7.5 | 0.43 |
| D3-vitamin | 4.4 | 0.25 |
| Total | 1729.9 | 100.00 |
| Coating liquid |  |  |
| Hypromellose 15 | 7.2 |  |
| Talc | 4.3 |  |
| Propylene glycol | 1.4 |  |
| Water, purified | 131.2 |  |
| Total | 1742.9 |  |

The granulate was compressed on a Fette PT 2090 using capsule shaped punches (9.4 mm×18.9 mm).

The tablets were coated in an O'Hara FC-660 (O'Hara), by use of the following parameters:

| | |
|---|---|
| Inlet air temperature | 50° C. |
| Product temperature | 45° C. |
| Pan rpm | 2.0 |
| Process air flow | 8000 m³ |
| Liquid flow rate | 300 g/min |
| batch size | 600 kg |

The obtained tablets had a crushing strength of 135 N and a disintegration time below 2 minutes.

Example 16

Impact on Sensoric Properties of the Use of Sugar Alcohols and Flavours
Kalcipos®-D
Ingredients according to the manufacturer:
Calcium carbonate
Vitamin D₃
Maltodextrin
Crosscarmellose sodium
Gelatine
Sucrose
Maize starch
Colloidal silicium dioxide
Magnesium stearate
Hypromellose
Macrogol 6000
Parafin
Hydrated soya bean oil
Hydrated cottonseed oil Sensorial comparison has been performed between the above described Kalcipos®-D and tablets manufactured as described in Example 15.

The test has been performed as a paired comparison test in accordance with ISO-5495, by use of 8 trained persons. This will show whether there is a significant difference between the reference (Kalcipos®-D) and the tablets of Example 15, at a five % level.

The products have been compared with respect to the following properties:
Sweetness
Lemon flavour
Chalkiness The results conformed a significant difference with respect to all three properties showing more sweetness, more lemon flavour and less chalkiness for the tablets of Example 15 when compared to Kalcipos®-D.

Example 17

Manufacture of Calcium Carbonate Containing Tablets
Tablets were manufactured according to Example 14 with the following formulations:

TABLE 17

| Raw material | [% w/w] |
|---|---|
| Calcium carbonate, Scoralite | 60-94 |
| Sorbitol 38 μm or Isomalt 27 μm | 5-30 |
| Cellulose microcryst Type 101 | 0-10 |
| Crosscarmellose sodium | 0-5 |
| Acesulfam Potassium | 0.1 |
| Flav. Lemon Powder 501162 | 0-2 |
| Magnesium stearate | 0.3-1 |

The individual amounts are adjusted so that each composition contains 1250 mg calcium carbonate and that the total amount does not exceed 100%. Tablets are compressed by use of punch design like:
Round shallow concave 16 mm
Round compound cup 14 mm
Capsule shaped 9.4×18.9 mm
Capsule shaped 8.6×18.9 mm
on a Fette PT 2090 achieving tablets with a crushing strength above 70 N and a disintegration time below 15 minutes for tablets containing croscarmellose sodium in an amount of approximately 0.5% or more (such tablets are meant for the oral route by swallowing). Optionally a standard water soluble coat (such as a traditional coating known by a person skilled in the art) can be applied to the tablets, in which case the disintegration time should be below 30 minutes.

If tablets only are meant for chewing the disintegration time is not relevant.

Example 18

Investigation of the Impact of Different Production Methods on the Size of Calcium Carbonate Tablets
This experiment was carried out in large production with a batch size of approx. 40.000 tablets. The experiment was performed in order to investigate whether the technique used for manufacturing granulate for the product had any impact on tablet dimensions especially the tablet height.

The techniques in question were:
i) Fluid bed granulation, and
ii) Roller compaction.

| | Raw material | Fluid bed Batch 1 per 1000 tabl. [g] | Roller compaction Batch 2 per 1000 tabl. [g] |
|---|---|---|---|
| I | Calcium carbonate Scoralite | 1250.0 | 1250.0 |
| II | Sorbitol 38 μm | — | 385.5 |
| III | Sorbitol 110 μm | 390.0 | — |
| IV | Povidone K 90 | 36.4 | — |
| V | Cellulose microcrystalline Type 101 | — | 75.0 |
| VI | Acesulfam Potassium | — | 1.0 |
| VII | Aspartame | 1.0 | |
| VIII | Flavour lemon | — | 7.5 |
| IX | Flavour granulate lemon | 50.68 | — |
| X | Magnesium stearate | 6.0 | 6.0 |
| XI | Purified water | 73.0 | — |
| | Tablet weight | 1734.08 | 1725.0 |

Manufacture of Batch 1:
The granulating fluid is manufactured by dissolving IV in XI. III is passed through a suitable screen and mixed with I in a Glatt fluid bed granulator. The powder mixture is granulated by spraying the granulating fluid on the powder bed while the fluidizing process is ongoing. The remaining parts of the excipients VII, IX and X are admixed to granulate and tablets are compressed by use of a Fette PT1090 and capsule shaped punch design (9.4×18.9 mm).

Manufacture of Batch 2
II is passed through a suitable screen and mixed together with I in a 220 l high shear mixer for 1 min at impeller speed 110 rpm and chopper speed 1500 rpm.

The powder mixture is granulated using a roller compactor according to example 1. The remaining excipients V, VI, VIII and X are admixed by use a high shear mixer (Diosna P250) with low impeller speed no chopper for 60 seconds and finally tablets are compressed by use of a Fette PT1090 and capsule shaped punch design (9.4×18.9 mm).

|  | Compression force [kN] | Tablet height [mm] | Tablet length [mm] |
|---|---|---|---|
| Batch 1 | 19.9 | 7.40 | 19.04 |
| Batch 2 | 20.9 | 7.16 | 19.07 |

Comparison of batch 1 and 2 shows that the lowest tablet height is obtained by roller compaction.

Example 19

Stability of Calcium Carbonate Tablets

This experiment was carried out in large production with a batch size of approx. 693,000 tablets. 3 batches were manufactured.

The experiment was performed in order to investigate the stability of coated tablets in open petri dishes and the reproducibility of crushing strength for three mixing intervals.

Composition: Amounts per tablet

TABLE 18

|  | [mg] | [%] |
|---|---|---|
| Raw material |  |  |
| Calcium carbonate, Scoralite | 1250 | 72.26 |
| Sorbitol 38 μm | 385 | 22.26 |
| Cellulose microcrystalline, type M101 | 56.0 | 3.24 |
| Crosscarmellose sodium | 20.0 | 1.16 |
| Acesulfam Potassium | 1.0 | 0.06 |
| Flavour Lemon | 7.5 | 0.43 |
| D3 vitamin | 4.4 | 0.25 |
| Magnesium stearate | 6.0 | 0.35 |
| Tablet weight [mg] | 1729.9 |  |
| Coating |  |  |
| Hypromellose 15 | 7.2 |  |
| Talc | 4.3 |  |
| Propylene glycol | 1.4 |  |
| Water, purified | 131.2 |  |
| Total weight [mg] | 1742.9 |  |

The batch was manufactured according to the following description:
Premixing and Roller Compaction Calcium Carbonate is added to a tumble mixer.

Sorbitol is sieved through screen size 2.0 mm and is transferred to the tumble mixer Calcium carbonate and sorbitol are premixed in the tumble mixer. Mixing time 15 minutes, speed 6 rpm.

The pre-mix is roller compacted with knurled rollers, screen size 1.5 mm. Settings: Gap 3.5 mm, Force 12 kN/cm, Roller speed 15 rpm.
Mixing The rest of the excipients, with the exception of magnesium stearate were admixed to the granulate in a tumble mixer using speed 6 rpm and mixing time for the 3 batches were according to Table 19.

TABLE 19

| | Mixing intervals | | |
|---|---|---|---|
| | Batch 1 | Batch 2 | Batch 3 |
| Mixing time | 20 minutes | 30 minutes | 40 minutes |

Magnesium stearate were admixed for 5 minutes, speed 6 rpm.
Tabletting

The granulate is compressed on a Fette 2090 tablet press by use of a capsule shaped punch design (18.9×9.4 mm) achieving a crushing strength of 110 N.
Coating Coating parameters is as described in Example 15.

The amount of film applied is corresponding to a theoretical weight gain of 0.75%.

Stability studies in open petri dishes stored at 25° C./60% RH have been performed. The results are shown in FIG. 22. Even though sorbitol having a mean particle size of 38 μm has been used a decrease is seen. This decrease is similar to that of tablets based on sorbitol 110 μm from Example 13. The decrease is due to the addition of extra excipients. However, the crushing strength is still sufficiently high to allow handling and therefore acceptable.

Example 20

Impact of Super Disintegrant on Water Absorption

A mixture of 72.26% calcium carbonate (Scoralite) and 22.26% sorbitol (38 μm) were Roller compacted as described in Example 18.

The roller compacted granulate was admixed the following ingredients:

TABLE 20

| | Composition of test 1 and 2 based on content of single tablets: | | |
|---|---|---|---|
| | Excipients | Test 1 | Test 2 |
| I | Roller compacted granulate from example 18 | 1635.5 mg | 1635.5 mg |
| II | Cellulose microcrystalline Type 101 | 75.0 mg | 75.0 mg |
| III | Croscarmellose sodium |  | 17.3 mg |
| VI | Magnesium stearate | 6.0 mg | 6.0 mg |
| | Tablet Weight: | 1733.8 mg | 1716.5 mg |

Tablets are compressed by use of capsule shaped punch design (9.4×18.9 mm)

Coating of the tablets is carried out based on the following composition

| | Excipients | % (w/w) |
|---|---|---|
| I | Hypromellose 15 | 2.5 |
| II | Talkum | 1.5 |
| III | Propylene Glycol | 0.5 |
| IV | Purified water | 95.5 |

Coating is carried out in a lab scale coater (Combi Cota, Niro, Denmark) using the following parameters:
Inlet air temperature: 48-50° C.
Liquid flow rate 3-4 gram/min
Spray pressure: 2 bar The tablets were tested in a DVS (Dynamic Vapour Sorption) equipment (Surface Measurement System, UK) at 25° C. and 60% RH. Each test was based on 5 tablets. The result is shown in FIG. 23. From FIG. 23 it can be seen that the addition of a superdisintegrant only results in a minor increase in water absorption meaning that only minor impact on stability of tablet technical properties is to be expected from the addition of a superdisintegrant.

The invention claimed is:

1. A solid dosage form comprising:
   a) a roller compacted granulate consisting of:
      i) one or more regularly shaped calcium-containing compounds as an active substance,
      ii) one or more pharmaceutically acceptable sugar alcohols having a micro structure selected from sorbitol and isomalt, wherein the one or more sugar alcohols have a mean particle size of at the most 150 micrometers, and
      iii) mannitol,
   wherein the roller compacted granulate has been prepared by roller compaction; and
   b) one or more pharmaceutically acceptable excipients, wherein the excipients are combined with the roller compacted granulate after roller compaction.

2. A solid dosage form according to claim 1 for oral administration.

3. A solid dosage form according to claim 1 in the form of a single unit or a multiple unit dosage form.

4. A solid dosage form according to claim 3 in the form of tablets, capsules, sachets, beads, pellets or the like.

5. A solid dosage form according to claim 4 in the form of tablets.

6. A solid dosage form according to claim 5, wherein the tablets have a shape and dimensions essentially as shown in FIG. 24 herein.

7. A solid dosage form according to claims 1 containing an amount of the one or more calcium-containing compounds corresponding to from about 250 to about 1000 mg calcium.

8. A solid dosage form according to claim 1, wherein the amount of the one or more calcium-containing compounds corresponds to from about 400 to about 600 mg calcium.

9. A solid dosage form according to claim 1, wherein the total concentration of the one or more calcium-containing compound in the dosage form is in a range of from about 40% to about 99% w/w.

10. A solid dosage form according to claim 1, wherein the total concentration of the roller compacted granulate contained in the dosage form is from about 65% to about 100% w/w.

11. A solid dosage form according to claim 1 containing from about 60% to about 95% w/w of the calcium-containing compound and from about 5% to about 40% w/w of the pharmaceutically acceptable sugar alcohol, provided that the sum does not exceed 100% w/w.

12. A solid dosage form according to claim 1 containing from about 60 to about 94% w/w of the calcium-containing compound, from about 5 to about 35% w/w of the pharmaceutically acceptable sugar alcohol and from about 1 to about 15% w/w of one or more pharmaceutically acceptable excipients and/or active substances, provided that the sum of ingredients amounts to 100% w/w.

13. A solid dosage form according to claim 1, wherein a SEM photo of a fractured surface of the solid dosage form shows that a surface of a deformed particle of sugar alcohol is in close contact with surfaces of the crystals of the one or more calcium-containing compound.

14. A solid dosage form according to claim 1 in the form of tablets, wherein the crushing strength of the tablets when stored in open petri dishes at 25° C. and 60% RH at the most changes 50% during a time period that starts 5 days after manufacture and runs during the remaining storage period of one month.

15. A solid dosage form according to claim 1 in the form of a chewable, suckable or swallowable tablet.

16. A solid dosage form according to claim 15, which has an acceptable taste with respect to sweetness, flavour and chalkiness when tested by a professional or skilled sensory test panel of at least 6 persons.

17. A solid dosage form according to claim 1 comprising a sweetener selected from the group consisting of dextrose, fructose, glycerin, glucose, isomalt, lactitol, lactose, maltitol, maltose, mannitol, sorbitol, sucrose, tagatose, trehalose, xylitol, alitame, aspartame, acesulfam potassium, cyclamic acid, cyclamate salt, neohesperidine dihydrochalcone, thaumatin, saccharin, saccharin salt, and mixtures thereof.

18. A solid dosage form according to claim 17 wherein the saccharin salt is selected from the group consisting of ammonium saccharin, calcium saccharin, potassium saccharin, and sodium saccharin.

19. A roller compacted granulate consisting of:
   i) one or more regularly shaped calcium-containing compounds as an active substance,
   ii) one or more pharmaceutically acceptable sugar alcohols having a micro structure selected from sorbitol and isomalt, wherein the one or more sugar alcohols have a mean particle size of at the most 150 micrometers, and
   iii) mannitol.

20. The roller compacted granulate according claim 19, wherein the one or more calcium-containing compound is in the form of crystals having a specific surface area below 1.5 $m^2/g$.

21. The roller compacted granulate according claim 19, wherein the concentration of the pharmaceutically acceptable sugar alcohol in the roller compacted granulate is at least 5% w/w.

22. The roller compacted granulate according claim 19, wherein the calcium-containing compound is calcium carbonate.

23. The roller compacted granulate according claim 19, wherein the content of the calcium-containing compound in the roller compacted granulate is in a range of from about 40% to about 100% w/w.

24. The roller compacted granulate according claim 19, containing from about 65% to about 80% w/w of the calcium-containing compound and from about 15% to about 25% w/w of sorbitol or isomalt or mixtures thereof.

25. A solid dosage form comprising:
   a) a roller compacted granulate consisting of:
      i) one or more regularly shaped calcium-containing compounds as an active substance,
      ii) one or more pharmaceutically acceptable sugar alcohols having a micro structure selected from sorbitol and isomalt, provided as dry particles, wherein the one or more sugar alcohols have a mean particle size of at the most 150 micrometers, and
      iii) mannitol,
   wherein the roller compacted granulate has been prepared by roller compaction; and
   b) one or more pharmaceutically acceptable excipients, wherein the excipients are combined with the roller compacted granulate after roller compaction.

* * * * *